US011547303B2

(12) United States Patent
Ruan et al.

(10) Patent No.: US 11,547,303 B2
(45) Date of Patent: Jan. 10, 2023

(54) NON-INVASIVE OPTICAL DETECTION SYSTEM AND METHOD OF MULTIPLE-SCATTERED LIGHT WITH SWEPT SOURCE ILLUMINATION

(71) Applicant: HI LLC, Los Angeles, CA (US)

(72) Inventors: Haowen Ruan, Los Angeles, CA (US); Adam Marblestone, Arlington, MA (US); Roarke Horstmeyer, Durham, NC (US); Yuecheng Shen, Guangzhou University (CN); Haojiang Zhou, Los Angeles, CA (US); Jamu Alford, Simi Valley, CA (US)

(73) Assignee: HI LLC, Los Angeles, CA (US)

( * ) Notice: Subject to any disclaimer, the term of this patent is extended or adjusted under 35 U.S.C. 154(b) by 638 days.

(21) Appl. No.: 16/393,002

(22) Filed: Apr. 24, 2019

(65) Prior Publication Data
US 2019/0336007 A1 Nov. 7, 2019

Related U.S. Application Data

(60) Provisional application No. 62/719,509, filed on Aug. 17, 2018, provisional application No. 62/666,963, filed on May 4, 2018.

(51) Int. Cl.
*A61B 5/00* (2006.01)

(52) U.S. Cl.
CPC .......... *A61B 5/0082* (2013.01); *A61B 5/4064* (2013.01)

(58) Field of Classification Search
CPC . A61B 8/0082; A61B 5/4064; A61B 2562/04; A61B 5/6814; A61B 5/066
See application file for complete search history.

(56) References Cited

U.S. PATENT DOCUMENTS 7,519,246 B2 4/2009 Welch et al.
8,654,320 B2 2/2014 Hasegawa et al.
(Continued)

FOREIGN PATENT DOCUMENTS

JP 2007114160 5/2007
WO WO2015109005 7/2015

OTHER PUBLICATIONS

Borycki, D., et al., "Reflectance-mode interferometric near-infrared spectroscopy quantifies brain absorption, scattering, and blood flow index in vivo" Opt. Lett., 2017. vol 42(3), p. 591-594 (Year: 2017).*
(Continued)

*Primary Examiner* — Keith M Raymond
*Assistant Examiner* — Sean A Frith
(74) *Attorney, Agent, or Firm* — Michael J. Bolan; Vista IP Law Group, LLP

(57) ABSTRACT

An optical source sweeps a source light over an optical wavelength range. An interferometer splits the source light into sample light and reference light, delivers the sample light into an anatomical structure, such that the sample light is scattered by the anatomical structure, resulting in physiological-encoded signal light that exits the anatomical structure, and combines the signal light and the reference light into an interference light pattern having an array of spatial components and a plurality of oscillation frequency components. An optical detector array detects intensity values of the array of spatial components. A processor derives an array of intensity values of each oscillation frequency component from the detected spatial component intensity value array, reduces each derived oscillation frequency component intensity value array to a single frequency component intensity value, and determines a depth of a physiological event in the anatomical structure based on the reduced frequency component intensity values.

43 Claims, 15 Drawing Sheets

(56) References Cited

U.S. PATENT DOCUMENTS

| | | | |
|---|---|---|---|
| 9,946,344 B2 | 4/2018 | Ayaz et al. | |
| 10,371,614 B2 | 8/2019 | Hosoda et al. | |
| 2003/0135101 A1* | 7/2003 | Webler | A61B 8/12 |
| | | | 600/407 |
| 2014/0187925 A1* | 7/2014 | Corl | G01S 15/8997 |
| | | | 600/425 |
| 2015/0304051 A1* | 10/2015 | Yuan | H04B 10/70 |
| | | | 398/188 |
| 2015/0304534 A1* | 10/2015 | Kadambi | G01S 17/894 |
| | | | 348/207.11 |
| 2016/0097632 A1* | 4/2016 | Sumiya | G01B 9/02044 |
| | | | 356/479 |
| 2016/0305914 A1* | 10/2016 | Wang | G02B 21/008 |
| 2016/0345880 A1 | 12/2016 | Nakaji et al. | |
| 2016/0350909 A1* | 12/2016 | Chu | G01N 21/00 |
| 2017/0172479 A1* | 6/2017 | Hirshfield | A61B 5/14553 |
| 2017/0227445 A1 | 8/2017 | Nakaji | |
| 2017/0234675 A1* | 8/2017 | Iddan | G01B 9/02004 |
| | | | 356/479 |
| 2018/0249911 A1 | 9/2018 | Hosoda et al. | |
| 2019/0133448 A1* | 5/2019 | Mak | G01B 9/02087 |

OTHER PUBLICATIONS

Atry, F., et al. "Monitoring Cerebral Hemodynamics Following Optogenetic Stimulation via Optical Coherence Tomography," IEEE Transactions on Biomedical Engineering. vol 62(2), 2015. p. 766-773 (Year: 2015).*

Borycki, D., et al., "Interferometric Near-Infrared Spectroscopy (iNIRS) for determination of optical and dynamical properties of turbid media," Optics Express. vol 24(1), 2015. p. 329-354 (Year: 2015).*

Sutin, J., et al., "Time-domain diffuse correlation spectroscopy," Optica. vol 3(9), 2016. p. 1006-1013 (Year: 2016).*

Choma, M., et al., "Instantaneous quadrature low-coherence interferometry with 3×3 fiber-optic couplers," Optics Letters. vol 28(22), 2003. p. 2162-2164 (Year: 2003).*

Lopez-Alonso, J., et al., "Characterization of spatial-temporal patterns in dynamic speckle sequences using principle component analysis," Optical Engineering. vol 55(12), 2016. p. 1-8 (Year: 2016).*

Svanberg, E., "Non-invasive optical monitoring of free and bound oxygen in humans," Department of Clinical Sciences Malmo, Anesthesiology and Intensive Care Medicine, Lund/Malmö. 2016. p. 1-109 (Year: 2016).*

Wenjun Zhou, et al., "Highly parallel, interferometric diffusing wave spectroscopy for monitoring cerebral blood flow dynamics", Optica, May 2018, vol. 5, No. 5 (10 pages).

Dawid Borycki, et al. "Reflectance-mode interferometric near-infrared spectroscopy quantifies brain absorption, scattering, and blood flow index in vivo", Opt. Lett. Feb. 1, 2017; 42(3): 591-594 (18 pages).

Dominik Wyser, et al., "Wearable and modular functional near-infrared spectroscopy instrument with multidistance measurements at four wavelengths", NEUROPHOTONICS, vol. 4, No. 04, Aug. 18, 2017, p. 1, XP055618655.

Hubin Zhao, et al., "Review of recent progress toward a fiberless, whole-scalp diffuse optical tomography system", NEUROPHOTONICS, vol. 5, No. 01, Sep. 26, 2017, p. 1, XP055619174.

Yanlu Li et al: "On-chip laser Doppler vibrometer for arterial pulse wave velocity measurement", Biomedical Optics Express, vol. 4, No. 7, Jun. 27, 2013 (Jun. 27, 2013), p. 1229, XP055619911.

Soren Aasmul et al: "Towards a compact multi-laser-beam device for cardiovascular screening", Retrieved from the Internet; Apr. 1, 2017 (Apr. 1, 2017 ), XP055619237; XP055619908.

Lefteris Gounaridis et al: "Design of grating couplers and MMI couplers on the TriPleX platform enabling ultra-compact photonic-based biosensors", Sensors and Actuators B: Chemical, vol. 209, Mar. 1, 2015 (Mar. 1, 2015), pp. 1057-1063, XP055619192.

Zhao Wang et al: "Silicon photonic integrated circuit swept-source optical coherence tomography receiver with dual polarization, dual balanced, in-phase and quadrature detection", Biomedical Optics Express, vol. 6, No. 7, Jun. 17, 2015 (Jun. 17, 2015), p. 2562, XP055620031.

C. Weimann et al: "Silicon photonic integrated circuit for fast and precise dual-comb distance metrology", Optics Express, vol. 25, No. 24, Nov. 16, 2017 (Nov. 16, 2017), p. 30091, XP055619005.

Artundo Inigo: "Photonic Integration : New Applications Are Visible", Mar. 1, 2017 (Mar. 1, 2017), XP055619204.

Wim Bogaerts: "Introduction to Silicon Photonics Circuit Design", Mar. 11, 2018 (Mar. 11, 2018 ), XP055617994.

Joost Brouckaert et al: "Integration of Photodetectors on Silicon Photonic Integrated Circuits (PICs) for Spectroscopic Applications", Oct. 25, 2010 (Oct. 25, 2010), XP055617942.

Marc Korczykowski, "Perfusion functional MRI reveals cerebral blood flow pattern under psychological stress", Departments of Radiology, Neurology, Psychiatry, and Psychology and Center for Functional Neuroimaging , University of Pennsylvania, Philadelphia, PA 19104; pp. 17804-17809, PNAS, Dec. 6, 2005, vol. 102, No. 49.

D. Borycki et al., "Interferometric Near-Infrared Spectroscopy (iNIRS) for determination of optical and dynamical properties of turbid media," Opt. Express 24 (2016).

M. A. Choma et al., "Sensitivity advantage of swept source and Fourier domain optical coherence tomography," Opt. Express 11 (2003).

Z. Cheng et al., "On-chip photonic synapse," Sci. Advances 3, e1700160 (2017).

Z. Wang et al., "Silicon photonic integrated circuit swept-source optical coherence tomography receiver with dual polarization, dual balanced, in-phase and quadrature detection," Biomed. Opt. Express 6 (2015).

D. Vermeulen, S. Selvaraja, P. Verheyen, G. Lepage, W. Bogaerts, P. Absil, D. Van Thourhout, and G. Roelkens, "High-efficiency fiber-to-chip grating couplers realized using an advanced CMOS-compatible silicon on-insulator platform," Opt. Express 18(17), 18278-18283 (2010).

C. Li et al, "Compact polarization beam splitter for silicon photonic integrated circuits with a 340-nm-thick silicon core layer", Opt. Letters (2017).

L. Chen, C. R. Doerr, L. Buhl, Y. Baeyens, and R. A. Aroca, "Monolithically integrated 40-wavelength demultiplexer and photodetector array on silicon," IEEE Photon. Technol. Lett. 23(13), 869-871 (2011).

C. T. Santis et al., "High coherence semiconductor lasers based on integral high-Q resonators in hybrid Si/III-V platforms," PNAS 111 (2014).

Gratton G., Fabiani M., "Fast-optical Imaging of Human Brain Function," Frontiers in Human Neuroscience, vol. 4, Article 52, pp. 1-9, Jun. 2010.

Eggegracht A. T., et al., "Mapping Distributed Brain Function and Networks with Diffuse Optical Tomography," Nature Photonics 8 (2014)).

Hill D.K. and Keynes, R.D., "Opacity Changes in Stimulated Nerve," J. Physiol., vol. 108, pp. 278-281 (1949).

Foust A.J. and Rector D.M., "Optically Teasing Apart Neural Swelling and Depolarization," Neuroscience, vol. 145, pp. 887-899 (2007)).

Scott A. Diddams, et al, "Molecular fingerprinting with the resolved modes of a femtosecond laser frequency comb", Nature Letters, vol. 445 Feb. 8, 2007.

Shijun Xiao and Andrew M. Weiner, "2-D wavelength demultiplexer with potential for > 1000 channels in the C-band", Optics Express, Jun. 28, 2004, vol. 12, No. 13.

M. Shirasaki, "Large angular dispersion by a virtually imaged phased array and its application to a wavelength demultiplexer", Optics Letters, vol. 21, No. 5, Mar. 1, 1996.

Kevin K. Tsia, "Simultaneous mechanical-scan-free confocal microscopy and laser microsurgery", Optics Letters, Jul. 15, 2009, vol. 34, No. 14.

(56) References Cited

OTHER PUBLICATIONS

S.R. Chinn and E.A. Swanson, "Optical coherence tomography using a frequency-tunable optical source", Optics Letters, Mar. 1, 1997, vol. 22, No. 5.
T. Bonin, G. Franke, M. Hagen-Eggert, P. Koch, and G. Hüttmann, "In vivo Fourier-domain full-field OCT of the human retina with 15 million A-lines/s," Optics Letters, Oct. 15, 2010, vol. 35, No. 20.
J. Fujimoto and E. Swanson, "The Development, Commercialization, and Impact of Optical Coherence Tomography.," Invest. Ophthalmol. Vis. Sci. 57, (Oct. 1-Oct. 13, 2016).
The Scientist and Engineer's Guide to Digital Signal Processing, "Chapter 9, Applications of the DFT", 16 pp.
Shoji Kishi, "Impact of swept cource optical coherence tomography on opthalmology", Department of Opthalmology, Gunma University Graduate School of Medicine, Maebashi, Japan, Sep. 29, 2015.
Wen Bao, et al., "Orthogonal dispersive spectral-domain optical coherence tomography", Optics Express, Apr. 21, 2014, vol. 22, No. 8.
PCT International Search Report and Written Opinion for International Appln. No. PCT/US2019/028881, Applicant HI LLC, forms PCT/ISA/210, 220 and 237 dated Sep. 18, 2019 (23 pages).

\* cited by examiner

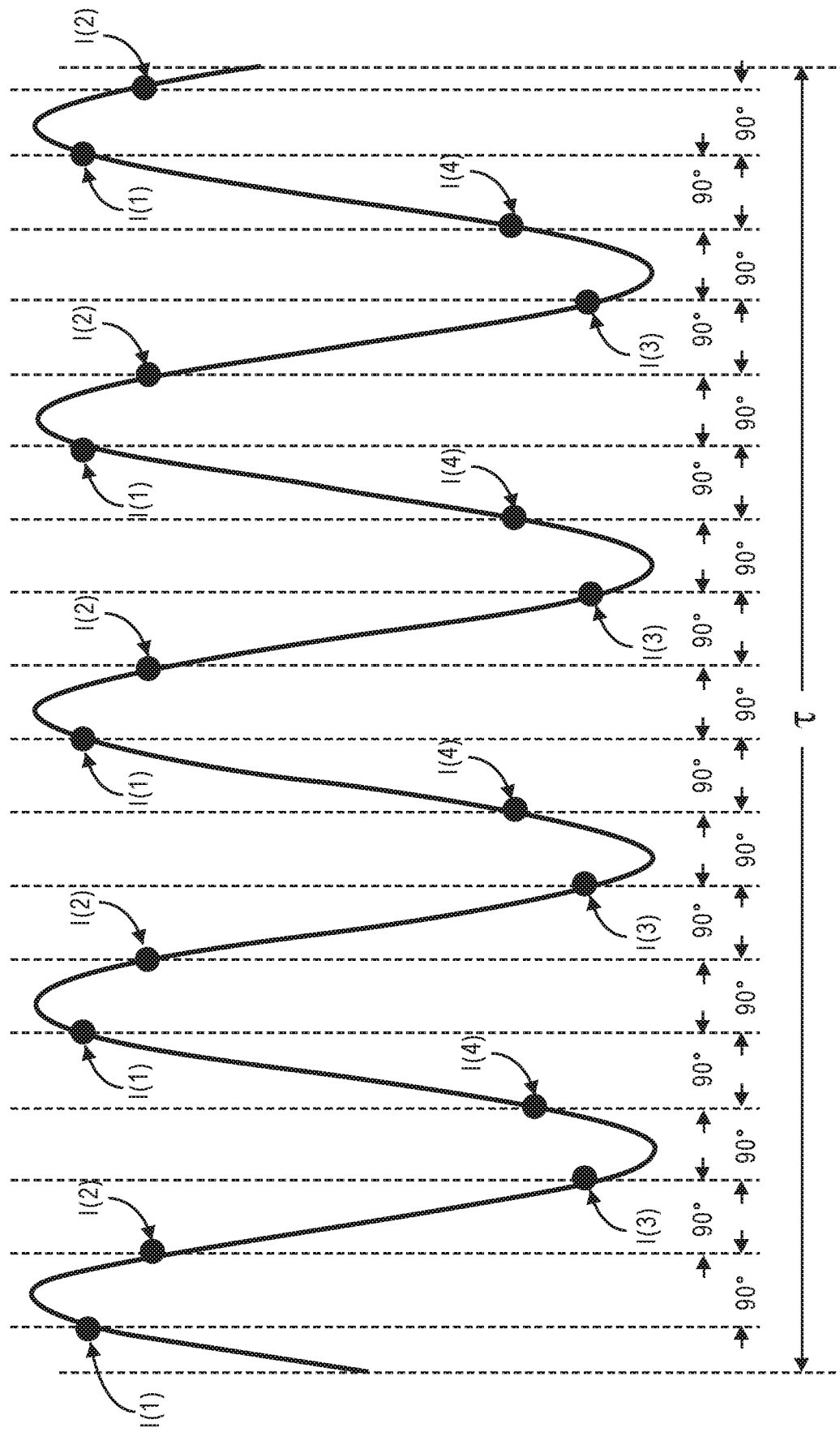

NON-INVASIVE OPTICAL DETECTION SYSTEM AND METHOD OF MULTIPLE-SCATTERED LIGHT WITH SWEPT SOURCE ILLUMINATION

RELATED APPLICATION DATA

Pursuant to 35 U.S.C. § 119(e), this application claims the benefit of U.S. Provisional Patent Application Ser. No. 62/666,963, filed May 4, 2018, and U.S. Provisional Patent Application Ser. No. 62/719,509, filed Aug. 17, 2018, which are expressly incorporated herein by reference.

FIELD OF THE INVENTION

The present inventions relate to methods and systems for non-invasive measurements in the human body, and in particular, methods and systems related to detecting physiologically-dependent optical parameters in the human body, e.g., the brain.

BACKGROUND OF THE INVENTION

Measuring neural activity in the brain is useful for medical diagnostics, neuromodulation therapies, neuroengineering, or brain-computer interfacing. Conventional methods for measuring neural activity in the brain include diffusive optical imaging techniques, which employ moderate amounts of near-infrared or visible light radiation, thus being comparatively safe and gentle for a biological subject in comparison to X-Ray Computed Tomography (CT) scans, positron emission tomography (PET), or other methods that use higher-energy and potentially harmful ionizing radiation. Moreover, in contrast to other known methods, such as functional magnetic resonance imaging (fMRI), these optically-based imaging methods do not require large magnets or magnetic shielding, and thus, can be scaled to wearable or portable form factors, which is especially important in applications, such as brain-computer interfacing.

However, because optical imaging techniques rely on light, which scatters many times inside brain, skull, dura, pia, and skin tissues, the light paths occurring in these techniques comprise random or "diffusive" walks, and therefore, only limited spatial resolution can be obtained by a conventional optical detector, often on the order of centimeters, with usable penetration depths being limited to a few millimeters. The reason for this limited spatial resolution is that the paths of photons striking the detector in such schemes are highly variable and difficult, and even impossible, to predict without detailed microscopic knowledge of the scattering characteristics of the brain volume of interest, which is typically unavailable in practice (i.e., in the setting of non-invasive measurements through skull for detecting neural activity in the brain for brain-computer interfacing). In summary, light scattering has presented challenges for optical detection techniques in achieving high spatial resolution deep inside tissue. Moreover, the diffusive nature of light propagation also creates challenges for measurements of fast changes in optical scattering inside tissue, since essentially all paths between source and detector are highly scattered to begin with.

One commercially available non-invasive imaging method, referred to as optical coherence tomography (OCT), is capable of acquiring images with high z-resolution (depth) (see James Fujimoto, et al., "The Development, Commercialization, and Impact of Optical Coherence Tomography," Investigative Ophthalmology & Visual Science, Vol. 57, OCT1-OCT13 (2016). Traditional OCT systems use coherent light (typically light in the near-infrared spectrum) to capture sub-surface images within optical scattering media (such as biological tissue) at a micrometer-resolution. The OCT system directs an optical beam at biological tissue and collects a small portion of the light that reflects from sub-surface features of the biological tissue. Although most of the light directed at the biological tissue is not reflected, but rather, diffusively scatters and contributes to background that may obscure the image, OCT utilizes a holographic (or interferometric) technique to select, via optical path selection, the photons that directly reflect off of the sub-surface features (i.e., the ballistic backscattered photons), and reject photons that scatter multiple times in the biological tissue before detection.

In particular, in a traditional OCT system, light from a light source is split into two paths along two different arms of an interferometer: a reference arm and a sample arm. In the sample arm, sample light is backscattered through a sample medium, and in the reference arm, reference light is back-reflected by a mirror where it recombines with the backscattered sample light at a coupler. Interference light is formed by any sample light that has an optical path length that matches, within the coherence length of the optical source, the optical path length traveled by the reference light. The intensity of the backscattering sample light having that optical path length can then be detected within the interference light.

Previous commercial OCT systems acquire data in the time domain (TD-OCT), and coherence gates the backscattered light from various depths in the biological tissue by adjusting the position of the mirror to tune the optical path length of the reference, such that only sample light having the matching optical path length is selected for detection at any given time. Current commercial OCT systems acquire data in the Fourier domain (FD-OCT), and do not involve adjusting the delay of the reference arm, and thus do not coherence gate, but rather involve acquiring an interferometric signal as a function of optical wavelength by combining the sample light and the reference light from a source with a finite spectral width at a fixed reference arm delay, and then Fourier-transforming the spectral or frequency-resolved interference as a function of photon time-of-flight to obtain the various depths in the biological tissue. It has been shown that FD-OCT has a significantly greater signal-to-noise (SNR) than FD-OCT (see Michael A. Choma, et al., "*Sensitivity Advantage of Swept Source and Fourier Domain Optical Coherence Tomography*," Optics Express, Vol. 11, No. 18, 8 Sep. 2003). Two distinct methods have been developed that employ the FD approach: (1) swept-source (SS-OCT), which time-encodes optical wavelengths by rapidly tuning a narrowband optical source through a broad optical bandwidth; and 2) spectral domain (SD-OCT), which uses a broadband light source to achieve spectral discrimination.

Regardless of the type, the depth at which a traditional OCT system images biological tissue is limited, because at greater depths the proportion of light that escapes without scattering (i.e., the ballistic light) is too small to be detected. Thus, the clinical applications of a traditional OCT system have, thus far, been limited to imaging sub-surface features, such as obtaining high-resolution ophthalmic images of the retina. As such, traditional OCT systems are presently insufficient for measuring neural activity in the regions of the brain at deeper depths (i.e., deeper than 2 mm).

Another type of diffusive optical imaging technique, referred to as interferometric Near-Infrared Spectroscopy (iNIRS) (see Borycki, Dawid, et al., "*Interferometric Near-Infrared Spectroscopy (iNIRS) for Determination of Optical and Dynamical Properties of Turbid Media*," Optics Express, Vol. 24, No. 1, Jan. 11, 2016), has been developed. While traditional OCT utilizes low-coherence interferometry to produce cross-sectional images of biological specimens with a resolution of few micrometers and an imaging range of 1-2 mm, the goal of iNIRS is to use high coherence interferometry to measure optical and dynamical properties of thick scattering media at a depth on the order of a few centimeters, at the cost of reduced axial resolution.

Furthermore, the systems described above have not been demonstrated to measure fast-optical signals, which refers to changes in optical scattering that occur when light propagating through active neural tissue (e.g., active brain tissue) is perturbed through a variety of mechanisms, including, but not limited to, cell swelling, cell volume change, changes in membrane potential, changes in membrane geometry, ion redistribution, birefringence changes, etc. (see Hill D. K. and Keynes, R. D., "*Opacity Changes in Stimulated Nerve*," J. Physiol., Vol. 108, pp. 278-281 (1949); Foust A. J. and Rector D. M., "*Optically Teasing Apart Neural Swelling and Depolarization*," Neuroscience, Vol. 145, pp. 887-899 (2007)). Because fast-optical signals are associated with neuronal activity, rather than hemodynamic responses, fast-optical signals may be used to detect brain activity with relatively high temporal resolution.

The current state of the art of iNIRS utilizes a single detector to measure the multiple-scattered photons from scattering samples, and therefore, has a limited data throughput, which leads to a lower SNR and detection speed. Furthermore, because only a single detector is used in an optical fiber-based system, a single mode fiber is used to deliver the light to the single detector, thereby reducing the light collection efficiency of the system, leading to a much lower SNR.

There, thus, remains a need to increase the data throughput and light collection efficiency of a swept source high coherence interferometry systems.

SUMMARY OF THE INVENTION

In accordance with a first aspect of the present inventions, a non-invasive optical measurement system comprises an optical source configured for sweeping a source light (e.g., having a spectral linewidth of less than 2 pm, and preferably less than 0.5 pm) over a range of optical wavelengths (e.g., an optical wavelength range greater than 3 pm, and preferably greater than 30 pm) during each of at least one measurement period. Each of the measurement period(s) may be equal to or less than a speckle decorrelation time of the anatomical structure. For example, each of the measurement period(s) may be equal to or less than 100 microseconds, and preferably, equal to or less than 10 microseconds.

The non-invasive optical measurement system further comprises an interferometer configured for splitting the source light into sample light and reference light, delivering the sample light into an anatomical structure, such that the sample light is scattered by the anatomical structure, resulting in physiological-encoded signal light that exits the anatomical structure, and combining, during each of the measurement period(s), the physiological-encoded signal light and the reference light into an interference light pattern having an array of spatial components and a plurality of oscillation frequency components. The plurality of oscillation frequency components are respectively encoded with a plurality of different depths of the anatomical structure. The interference light pattern may be a speckle light pattern, in which case, the spatial components may be speckle grains. The non-invasive optical measurement system further comprises an optical detector array configured for detecting intensity values of the array of spatial components of the interference light pattern during each of the measurement period(s).

The non-invasive optical measurement system further comprises a processor configured for sequentially deriving an array of intensity values of each oscillation frequency component of the interference light pattern over the optical detector array from the detected spatial component intensity value array of the interference light pattern during the measurement period(s), reducing each derived oscillation frequency component intensity value array to a single frequency component intensity value (e.g., by computing a mean of the respective derived oscillation frequency component intensity value array), and determining a depth of a physiological event in the anatomical structure, at least partially, based on the reduced frequency component intensity values (e.g., by comparing the reduced oscillation frequency component intensity values to corresponding reference oscillation frequency component intensity values). By way of non-limiting example, the anatomical structure may be a brain, in which case, the physiological event may be indicative of neural activity, e.g., a fast-optical signal.

In one embodiment, the measurement period(s) comprises a single measurement period, in which case, the processor may be configured for sequentially deriving each oscillation frequency component intensity array over the optical detector array from the detected spatial component intensity value array of the interference light pattern during the single measurement period by computing a Fourier transform of the detected spatial component intensity value array of the interference light pattern. In this case, the non-invasive optical measurement system may further comprise a charged coupled device (CCD) camera comprising the optical detector array.

In another embodiment, the measurement period(s) comprises a plurality of measurement periods, in which case, the processor may be configured for sequentially deriving each oscillation frequency component intensity value array over the optical detector array from the detected spatial component intensity value array of the interference light pattern during each respective one of the measurement periods. The processor may, e.g., be configured for sequentially deriving each oscillation frequency component intensity value array over the optical detector array from the detected spatial component intensity value array of the interference light pattern during each respective one of the measurement periods by locking in each oscillation frequency component during each respective one of the measurement periods, e.g., by accumulating at least two sequential ones of the intensity values detected during each cycle of the respective oscillation frequency component respectively in at least two bins, and performing a function on the accumulated contents of the at least two bins. If there are only two bins, the function may be, e.g., computing the difference between the accumulated contents of the two bins. If there are only four bins, the function may be, e.g., computing a quadrature of the accumulated contents of the four bins. In this embodiment, the non-invasive optical measurement system may further comprise a lock-in camera that includes the optical detector array and a portion of the processor that is configured for locking in each oscillation frequency component during each respective one of the measurement periods, and a central processing unit (CPU) that includes another portion of the processor that is configured for reducing the derived array of intensity values of each oscillation frequency component to the single frequency component value, and determining the depth of the physiological event in the anatomical structure, at least partially, based on the reduced frequency component values.

In accordance with a second aspect of the present inventions, a non-invasive optical measurement method comprises sweeping a source light (e.g., having a spectral linewidth of less than 2 pm, and preferably less than 0.5 pm) over a range of optical wavelengths (e.g., an optical wavelength range greater than 3 pm, and preferably greater than 30 pm) during each of at least one measurement period. Each of the measurement period(s) may be equal to or less than a speckle decorrelation time of the anatomical structure. For example, each of the measurement period(s) may be equal to or less than 100 microseconds, and preferably, equal to or less than 10 microseconds.

The non-invasive optical measurement method further comprises splitting the source light into sample light and reference light, and delivering the sample light into an anatomical structure, such that the sample light is scattered by the anatomical structure, resulting in physiological-encoded signal light that exits the anatomical structure, and combining, during each of the measurement period(s), the physiological-encoded signal light and the reference light into an interference light pattern having an array of spatial components and a plurality of oscillation frequency components. The plurality of oscillation frequency components are respectively encoded with a plurality of different depths of the anatomical structure. The interference light pattern may be a speckle light pattern, in which case, the spatial components may be speckle grains.

The non-invasive optical measurement method further comprises detecting intensity values of the array of spatial components of the interference light pattern during each of the measurement period(s), sequentially deriving an array of intensity values of each oscillation frequency component of the interference light pattern from the detected spatial component intensity value array of the interference light pattern during the measurement period(s), reducing each derived oscillation frequency component intensity value array to a single oscillation frequency component intensity value (e.g., by computing a mean of the respective derived oscillation frequency component intensity value array), and determining a depth of a physiological event in the anatomical structure, at least partially, based on the reduced oscillation frequency component intensity values (e.g., by comparing the reduced oscillation frequency component intensity values to corresponding reference oscillation frequency component intensity values). By way of non-limiting example, the anatomical structure may be a brain, in which case, the physiological event may be indicative of neural activity, e.g., a fast-optical signal.

In one optical measurement method, the measurement period(s) comprises a single measurement period, and each oscillation frequency component intensity value array is derived from the detected spatial component intensity value array of the interference light pattern during the single measurement period by computing a Fourier transform of the detected spatial component intensity value array of the interference light pattern. In this case, the spatial component intensity value array of the interference light pattern may be detected during each of the measurement period(s) using a charged coupled device (CCD) camera.

In another non-invasive optical measurement method, the measurement period(s comprises a plurality of measurement periods, and each oscillation frequency component intensity value array is derived from the detected spatial component intensity value array of the interference light pattern during each respective one of the measurement periods. Each oscillation frequency component intensity value array may be sequentially derived from the detected spatial component intensity value array of the interference light pattern during each respective one of the measurement periods by locking in each oscillation frequency component during each respective one of the measurement periods, e.g., by accumulating at least two sequential ones of the intensity values detected during each cycle of the respective oscillation frequency component respectively in at least two bins, and performing a function on the accumulated contents of the at least two bins. If there are only two bins, the function may be, e.g., computing the difference between the accumulated contents of the two bins. If there are only four bins, the function may be, e.g., computing a quadrature of the accumulated contents of the four bins.

In accordance with a third aspect of the present inventions, a non-invasive optical measurement system comprises an optical source configured for sweeping a source light (e.g., having a spectral linewidth of less than 2 pm, and preferably less than 0.5 pm) over a range of optical wavelengths (e.g., an optical wavelength range greater than 3 pm, and preferably greater than 30 pm) during each of at least one measurement period. Each of the measurement period(s) may be equal to or less than a speckle decorrelation time of the anatomical structure. For example, each of the measurement period(s) may be equal to or less than 100 microseconds, and preferably, equal to or less than 10 microseconds.

The non-invasive optical measurement system further comprises an interferometer configured for splitting the source light into sample light and reference light, delivering the sample light into an anatomical structure, such that the sample light is scattered by the anatomical structure, resulting in physiological-encoded signal light that exits the anatomical structure, and combining, during each of the measurement period(s), the physiological-encoded signal light and the reference light into an interference light pattern having an array of spatial components and a plurality of oscillation frequency components. The plurality of oscillation frequency components are respectively encoded with a plurality of different depths of the anatomical structure. The interference light pattern may be a speckle light pattern, in which case, the spatial components may be speckle grains.

The non-invasive optical measurement system further comprises a lock-in camera configured for detecting intensity values of the array of spatial components of the interference light pattern during each of the plurality of measurement periods, sequentially locking in the oscillation frequency components respectively during the plurality of measurement periods, and outputting an array of intensity values of each oscillation frequency component of the interference light pattern over the optical detector array.

The non-invasive optical measurement system further comprises a processor (e.g., a central processing unit (CPU)) configured for determining a depth of a physiological event in the anatomical structure, at least partially, based on the outputted oscillation frequency components intensity value arrays. In one embodiment, the processor is configured for reducing each outputted oscillation frequency component intensity value array to a single frequency component value, and determining the depth of a physiological event in the anatomical structure, at least partially, based on the reduced oscillation frequency component intensity values (e.g., by computing a mean of the respective outputted oscillation frequency component intensity value array). By way of non-limiting example, the anatomical structure may be a brain, in which case, the physiological event may be indicative of neural activity, e.g., a fast-optical signal.

In accordance with a fourth aspect of the present inventions, a non-invasive optical measurement method comprises sweeping a source light (e.g., having a spectral linewidth of less than 2 pm, and preferably less than 0.5 pm) over a range of optical wavelengths (e.g., an optical wavelength range greater than 3 pm, and preferably greater than 30 pm) during each of at least one measurement period. Each of the measurement period(s) may be equal to or less than a speckle decorrelation time of the anatomical structure. For example, each of the measurement period(s) may be equal to or less than 100 microseconds, and preferably, equal to or less than 10 microseconds.

The non-invasive optical measurement method further comprises splitting the source light into sample light and reference light, and delivering the sample light into an anatomical structure, such that the sample light is scattered by the anatomical structure, resulting in physiological-encoded signal light that exits the anatomical structure, and combining, during each of the measurement period(s), the physiological-encoded signal light and the reference light into an interference light pattern having an array of spatial components and a plurality of oscillation frequency components. The plurality of oscillation frequency components are respectively encoded with a plurality of different depths of the anatomical structure. The interference light pattern may be a speckle light pattern, in which case, the spatial components may be speckle grains.

The non-invasive optical measurement method further comprises detecting intensity values of the array of spatial components of the interference light pattern during each of the measurement period(s), sequentially locking in the oscillation frequency components respectively during the plurality of measurement periods, outputting an array of intensity values of each oscillation frequency component, and determining a depth of a physiological event in the anatomical structure, at least partially, based on the outputted oscillation frequency components intensity value arrays. The non-invasive optical measurement method may further comprise reducing each outputted oscillation frequency component intensity value array to a single frequency component value, in which case, the depth of the physiological event in the anatomical structure may be determined, at least partially, based on the reduced oscillation frequency component intensity values (e.g., by computing a mean of the respective outputted oscillation frequency component intensity value array).

In accordance with a fifth aspect of the present inventions, a non-invasive optical measurement system comprises an optical source configured for generating source light during each of at least one measurement period. Each of the measurement period(s) may be equal to or less than a speckle decorrelation time of the anatomical structure. For example, each of the measurement period(s) may be equal to or less than 100 microseconds, and preferably, equal to or less than 10 microseconds.

The non-invasive optical measurement system further comprises an interferometer configured for splitting the source light into sample light and reference light, delivering the sample light into an anatomical structure, such that the sample light is scattered by the anatomical structure, resulting in physiological-encoded signal light portions that respectively exit different spatial regions of the anatomical structure, and respectively combining, during each of the measurement period(s), the physiological-encoded signal light portions and the reference light into a plurality of interference light patterns, each having spatial components. Each of the interference light patterns may be a speckle light pattern, in which case, the spatial components may be speckle grains.

The non-invasive optical measurement system further comprises an optical detector array having a plurality of sub-arrays respectively configured for respectively detecting intensity values of the array of spatial components of the interference light patterns during each of the measurement period(s), and a processor configured for determining a three-dimensional location of the physiological event in the anatomical structure based on the detected spatial component intensity value arrays of the respective interference light patterns. By way of non-limiting example, the anatomical structure may be a brain, in which case, the physiological event may be indicative of neural activity, e.g., a fast-optical signal.

In one embodiment, the optical source is configured for sweeping the source light over a range of optical wavelengths for each of the measurement period(s), each of the interference light patterns has oscillation frequency components respectively encoded with different depths of the anatomical structure, and the processor is configured for sequentially deriving an array of intensity values of each oscillation frequency component of the respective interference light pattern over each sub-array of the optical detector array from the detected spatial component intensity value array of the interference light patterns during the at least one measurement period, reducing each derived oscillation frequency component intensity array to a single oscillation frequency component intensity value for each of the sub-arrays of the optical detector array (e.g., by computing a mean of the respective derived oscillation frequency component intensity value array), and determining a depth of the physiological event in the anatomical structure, at least partially, based on the reduced oscillation frequency component intensity values.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings.

Understanding that these drawings depict only typical embodiments of the invention and are not therefore to be considered limiting of its scope, the invention will be described and explained with additional specificity and detail through the use of the accompanying drawings in which:

FIG. 10B is a timing diagram illustrating another method used by the lock-in camera of FIG. 9 to lock in an oscillation frequency component;

DETAILED DESCRIPTION OF THE EMBODIMENTS

Figure 1:
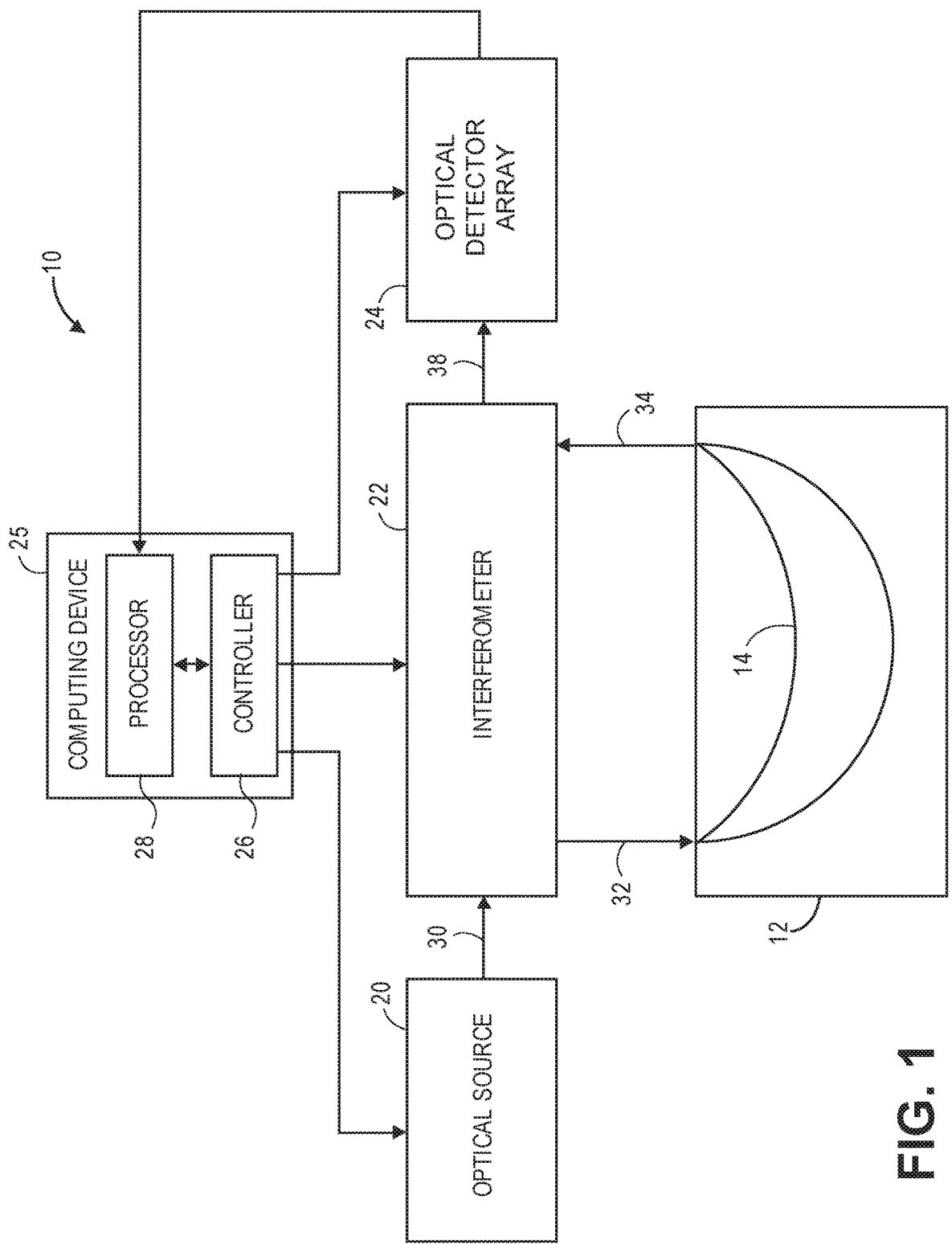
FIG. 1 is a block diagram of a non-invasive optical measurement system constructed in accordance with one embodiment of the present inventions.

The embodiments of the non-invasive optical measurement systems described herein are swept-source holographic optical systems (i.e., systems that mix detected signal light against reference light in order to increase the signal-to-noise ratio (SNR) of the relevant signal), and in particular interferometric Near-Infrared Spectroscopy (iNIRS) systems. As such, the non-invasive optical measurement systems described herein are focued on the measurement of multiple-scattered signal light of different depth-correlated optical path lengths, as opposed to ballistic or single-scattered signal light measured by a conventional Optical Coherence Tomography (OCT) system or a swept-source OCT (SS-OCT) system, and therefore, are capable of detecting physiological events in tissue, e.g., brain tissue, at a penetration depth of multiple centimeters.

Unlike a conventional iNIRS system, which has a limited data throughput due to its single detector measurement of the multiple-scattered photons, and thus has a lower signal-to-noise (SNR) and detection speed, the non-invasive optical measurement systems described herein use an optical detector array to achieve parallel detection of the multiple-scattered signal light, thereby enabling higher data throughput, and thus a higher SNR and detection speed. This should be contrasted with conventional OCT systems, which may utilize optical detector arrays in the form of camera pixels, but do so for a completely different purpose. That is, the non-invasive optical measurement systems described herein utilize an optical detector array to determine an optical path length between the optical source and optical detector for the purposes of functional measurements, e.g., localizing neural activity in an anatomical structure, and its use of many camera pixels serves the purpose of increasing signal to noise ratio for such functional measurements in deeper tissue depths, whereas the camera-based OCT approach, such as "full field OCT," utilizes an optical detector array to acquire actual images of the anatomical structure, and its use of many camera pixels, does not increase signal to noise ratio, but rather allows parallel imaging of many anatomical locations, and furthermore which is, unlike the optical measurement systems described herein, not able to probe deeper depths at targeted tissue because of its reliance on ballistic or single scattered light, whereas the present invention provides for detection of multiple scattered light. The non-invasive optical measurement systems described herein may be implemented as optical fiber-based systems, in which case, the optical detector array enables the use of a multi-mode optical fiber and/or bundles of optical fibers, which allows the collection of photons on orders of magnitude greater than that collected by a single detector via a single-mode optical fiber, thereby boosting the light collection efficiency, and leading to an even higher SNR.

In a particular embodiment of the non-invasive optical measurement system described in further detail below, the parallel detection scheme is facilitated by employing a lock-in camera that detects only one temporal frequency component of the detected swept source interference intensity signal from the multiple-scattered signal light at a time. Although it reduces the detection speed over the entire range of optical path lengths of the signal light, such embodiment of the non-invasive optical measurement system enables detection of the higher temporal frequency components in the detected swept source interference signal that conventional cameras with limited detection speed cannot capture, enabling improved depth selectivity and sensitivity to small neural signals detected within the tissue. This results in improved signal to noise ratio compared with conventional iNIRS approaches that rely on single fast-sampling detectors. The present techniques enable multi-pixel detection of the rapidly varying swept source interference signal, thus allowing a large number of photons to be collected from a given source-detector pair without destructive interference, whereas a single large and fast-sampling detector would be subject to destructive interference limiting the detected signal magnitude. Also, a conventional camera would be too slow to detect the rapidly varying swept source interference signal. The use of lock-in detection, to implement this improved signal to noise ratio with many-pixel detection of the swept source interference signal, necessitates a multi-step measurement in which one temporal frequency component of the detected swept source interference intensity signal from the multiple-scattered signal light is detected at a time, and such temporal frequency components are detected serially in rapid succession during a measurement period of neural activity, such as within a duration of 100 milliseconds or less.

In another particularly advantageous embodiment, the optical detector array is partitioned into discrete regions to simultaneously detect the multiple-scattered signal light from various discrete regions of the anatomical structure, thereby allowing relevant physiological events to be simultaneously observed.

Referring now to FIG. 1, a generalized embodiment of a non-invasive optical measurement system 10 constructed in accordance with the present inventions will now be described. The non-invasive optical measurement system 10 is designed to non-invasively acquire physiological-encoded signal light (i.e., signal light representative of a physiologically-dependent optical parameter) in an anatomical structure 12, processing the physiological-encoded signal light, and determining the presence and depth of a physiological event in the anatomical structure 12 based on the processed physiological-encoded signal light.

In the illustrated embodiment, the anatomical structure 12 is a brain, in which case, the non-invasive optical measurement system 10 may identify the presence and location of neural activity within the brain 12. Although for exemplary purposes, The non-invasive optical measurement system 10 is described as acquiring physiological-encoded data from brain tissue, variations of such optical measurement system 10 may be used to acquire physiological-encoded data from other anatomical structures of a human body, animal body and/or biological tissue.

In the illustrated embodiments, the physiological-encoded data acquired by The non-invasive optical measurement system 10 is neural-encoded data, and the physiological event is a fast-optical signal. Fast-optical signal refers to changes in optical scattering that occur when light propagating through active neural tissue (e.g., active brain tissue) is perturbed through a variety of mechanisms, including, but not limited to, cell swelling, cell volume change, changes in membrane potential, changes in membrane geometry, ion redistribution, birefringence changes, etc. Fast-optical signals are associated with neuronal activity, rather than hemodynamic responses, and fast-optical signals may be used to detect brain activity with relatively high temporal resolution. Although in alternative embodiments, the physiological event may be a slower hemodynamic change, e.g., Doppler shift due to moving blood flow, changes in blood volume, metabolism variations such a blood oxygen changes. However, as will be described in further detail below, the non-invasive optical measurement system 10, when properly tuned to a specific type of physiological event, is capable of decoding light propagating through the brain to detect any physiological event that causes a change in an optical property of the brain 12.

The neural activity information (or the acquired neural-encoded data from which it is derived) may be transmitted to external programmable devices for use (e.g., computed, processed, stored, etc.) therein, e.g., medical devices, entertainment devices, neuromodulation stimulation devices, lie detection devices, alarm systems, educational games, brain interface devices, vehicle's audio systems, vehicle's autonomous driving systems, etc., and/or may be used internally to adjust the detection parameters of The non-invasive optical measurement system 10, such as increasing or decreasing the strength of the optical source and/or data compression and/or analysis, such a Fast Fourier Transform (FFT) and/or statistical analysis.

Although the non-invasive optical measurement system 10, for purposes of brevity, is described herein as acquiring neural-encoded data from the brain 12 by using a single fixed source/detector-array pair arrangement to create one bundle of detected optical paths 14 through the brain 12 in a single measurement period, in a practical implementation capable of localizing the fast-optical signal in an x-y plane along the surface of the brain 12, variations of the non-invasive optical measurement system 10 may utilize more complex source-detector arrangements (e.g., single-source multi-detector, multi-source single-detector, or multi-source multi-detector) to simultaneously create multiple sample paths spatially separated from each other within the brain 12 in a single measurement period, or may utilize a movable source-detector arrangement to sequentially create multiple sample paths over several measurement periods, as described in U.S. Provisional Patent Application Ser. No. 62/692,074, entitled "Frequency Domain Optical Spectroscopy For Neural Decoding," U.S. patent application Ser. No. 16/379,090, entitled "Non-Invasive Frequency Domain Optical Spectroscopy For Neural Decoding," and U.S. Provisional Patent Application Ser. No. 62/692,124, entitled "Interferometric Frequency-Swept Source and Detector in a Photonic Integrated Circuit," which are expressly incorporated herein by reference. Thus, in a practical implementation, the non-invasive optical detection system 10 may detect and localize physiological events associated with neural activity in the brain, including fast-optical signals, in three-dimensions, with two of the dimensions represented as an x-y plane spanning the surface of the brain 12 encoded within the spatially separated multiple sample paths and the third dimension (z-dimension or depth into the brain 12) being encoded within frequency components of photons propagating along the sample paths.

Referring still to FIG. 1, the non-invasive optical measurement system 10 generally comprises an optical source 20, an interferometer 22, an array of optical detectors 24, a computing device or other similar device 25, which all operate together to non-invasively detect the presence and depth of a fast-optical signal in the brain 12.

The computing device 25 comprises a controller 26, a processor 28, a memory (not shown), a display (not shown), and an input device (not shown). The computing device 25 can, e.g., be a computer, tablet, mobile device, or any other suitable device for processing information. The computing device 25 can be local to the user or can include components that are non-local to the user. For example, in at least some embodiments, the user may operate a terminal that is connected to a non-local computing device. In other embodiments, the memory can be non-local to the user. The computing device 25 can utilize any suitable processor 28, including one or more hardware processors that may be local to the user or non-local to the user or other components of the computing device 25. The processor 28 is configured to execute instructions provided to the processor 28, as described below.

Any suitable memory can be used for the computing device 25. The memory can be a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal. The term "modulated data signal" can include a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display can be any suitable display device, such as a monitor, screen, or the like, and can include a printer. In some embodiments, the display is optional. In some embodiments, the display may be integrated into a single unit with the computing device 25, such as a tablet, smart phone, or smart watch. The input device can be, for example, a keyboard, mouse, touch screen, track ball, joystick, voice recognition system, or any combination thereof, or the like.

Although the controller 26 and processor 28 are described herein as being separate components, it should be appreciated that portions or all functionality of the controller 26 and processor 28 may be performed by a single component. Furthermore, although all of the functionality of the controller 26 is described herein as being performed by a single component, and likewise all of the functionality of the processor 28 is described herein as being performed by a single component, such functionality each of the controller 26 and the processor 28 may be distributed amongst several computing devices. Moreover, it should be appreciated that those skilled in the art are familiar with the terms "controller" and "processor," and that they may be implemented in software, firmware, hardware, or any suitable combination thereof.

In this embodiment, only a single source-detector arrangement is described, although as discussed above, The non-invasive optical measurement system 10 may employ a complex source-detector arrangement. The optical source 20 is configured for generating source light 30, and may take the form of a distributed feedback (DFB) laser, although other light sources, e.g., a super luminescent diode (SLD), a light emitting diode (LED), a diode-pumped solid-state (DPSS) laser, a laser diode (LD), a super luminescent light emitting diode (sLED), a titanium sapphire laser, and/or a micro light emitting diode (m LED), or similar laser to achieve very narrow spectral linewidths and extremely high amplitude stability, among other optical sources, may be used.

The optical source 20 may have either a predefined coherence length or a variable coherence length. Since the goal of the non-invasive optical measurement system 10 is to measure optical and dynamic properties deeper in depth within brain tissue, as opposed to acquiring images of the brain tissue at a shallow depth by traditional OCT systems, the optical source 20 preferably has an instantaneous spectral linewidth and tuning range narrower by several orders of magnitude than in traditional OCT systems, enabling the measurement of distinctly longer optical path lengths (of up to tens of centimeters) at the cost of reduced resolution (of the order of millimeters). Preferably, the optical source 30 has a coherence length of at last 30 cm, an instantaneous spectral linewidth of less than 2 nm, and preferably less than 0.5 nm, and an optical wavelength range greater than 3 pm, and preferably greater than 30 pm.

The source light 30 may be ultraviolet (UV) light, visible light, and/or near-infrared and infrared light, and may have any suitable wavelength, e.g., in the range of 350 nm-1800 nm. The source light 30 may be close to monochromatic in nature, comprising approximately a single-wavelength light, or the source light 30 may have multiple wavelengths (e.g., white light). As discussed in further detail below, the source light 30 has a narrow optical spectrum that is rapidly swept (e.g., changed over time) to functionally mimic or create an effective broad optical spectrum.

Notwithstanding the foregoing, it is preferred that the optical wavelength of the source light 30 be selected to maximize sensitivity to the specific physiological event of interest. For example, in the preferred case where the physiological event of interest is the presence of a fast-optical signal, an optical wavelength greater than hemoglobin absorption wavelengths (e.g., greater than 850 nm) may be used for the source light 30 to detect scattering changes by materials other than blood, and/or to detect scattering by blood outside of wavelengths that are strongly absorbed by blood. Optionally, an optical wavelength equal to or greater than 1000 nm may be used for the source light 30 to maximize penetration. In the additional or alternative case where the physiological event of interest is a change in the blood oxygen concentration, an optical wavelength in the range of 550 nm to 850 nm may be used for the source light 30. Multiple optical wavelengths can be used for the source light 30 to allow different physiological events to be distinguished from each other. For example, source light 30 having two optical wavelengths of 900 nm and 700 nm can be respectively used to resolve fast-optical signals and blood oxygenation. Alternatively, the wavelength of the source light 30 can be selected to maximize the detector sensitivity.

The controller 26 instructs the optical source 20 to sweep the source light 30 over a range of optical path lengths. The optical source 20 may receive input current from a drive circuit (not shown), e.g., a laser diode current driver. The controller 26 may modulate such input current using a sinusoidal waveform having a suitable frequency, e.g., 50 KHz. The sweep rate of the optical source 20 defines a measurement period of the non-invasive optical measurement system 10 in accordance with the equation:

[1] $\tau = 1/R$, where $\tau$ is the measurement period, and $R$ is the uni-directional rate (forward sweep or reverse sweep).

Figure 2:
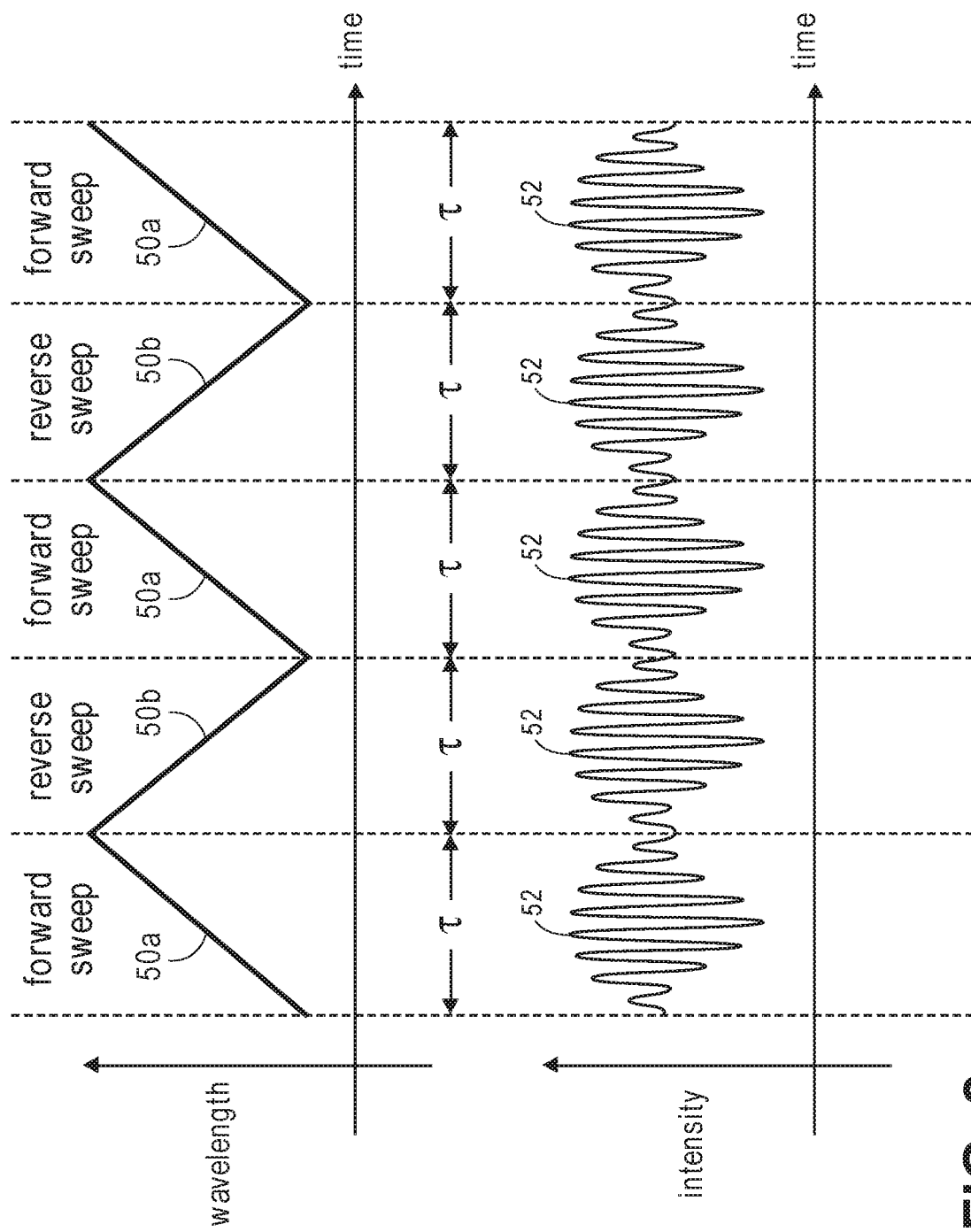
FIG. 2 is a timing diagram illustrating the optical sweeps performed by the non-invasive optical measurement system of FIG. 1, and fringe patterns in interference light patterns resulting from the optical sweeps.

As illustrated in FIG. 2, the optical source 20 sweeps across a range of optical wavelengths during the measurement period $\tau$. In the illustrated embodiment, the measurement periods z are respectively defined by both forward sweeps 50a (low to high wavenumbers) and rearward sweeps 50b (high to low wave numbers) of the optical source 20, thereby maximizing the usage of the full sweep range of the optical source 20. However, in alternative embodiments, all of the measurement periods z are defined by either forward sweeps 50a or reverse sweeps 50b (but not both), such that there are idle time intervals between sequential measurement periods z equal to the time period of a unilateral sweep R. However, because the data throughput is generally limited by the detection and processing scheme, the existence of the idle time intervals between the measurement periods z will generally not limit the data throughput of The non-invasive optical measurement system 10.

Notwithstanding this, the uni-directional sweep rate R of the optical source 20 may be any suitable rate, but preferably, defines a measurement period z equal to or less than the speckle decorrelation time (which is due to the scatterers' motion inside tissue, and rapidly decreases with the depth of the tissue, and in particular, scales super-linearly with the depth into tissue, falling to microseconds or below as the tissue depth extends to the multi-centimeter range) of brain tissue. For example, the measurement period z may be equal to or less than 100 μs (equivalent to a uni-directional sweep rate of 10 KHz), and preferably equal to or less than 10 μs (equivalent to a uni-directional sweep rate of 100 KHz).

The interferometer 22 is configured for splitting the source light 30 from the optical source 20 into sample light 32, which is delivered to the brain 12 along a sample arm optical fiber 40b and exits the brain 12 as physiological-encoded (in this case, neural-encoded) signal light 34, and reference light 36 (shown in FIG. 3), which propagates along a reference arm optical fiber 40c outside of the brain 12. The interferometer 22 is further configured for combining the neural-encoded signal light 34 with the reference light 36 to create an interference light pattern 38 (in this case, an interference light speckle pattern) having an array of spatial components (in this case, speckle light grains) and a plurality of oscillation frequency components.

Figure 3:
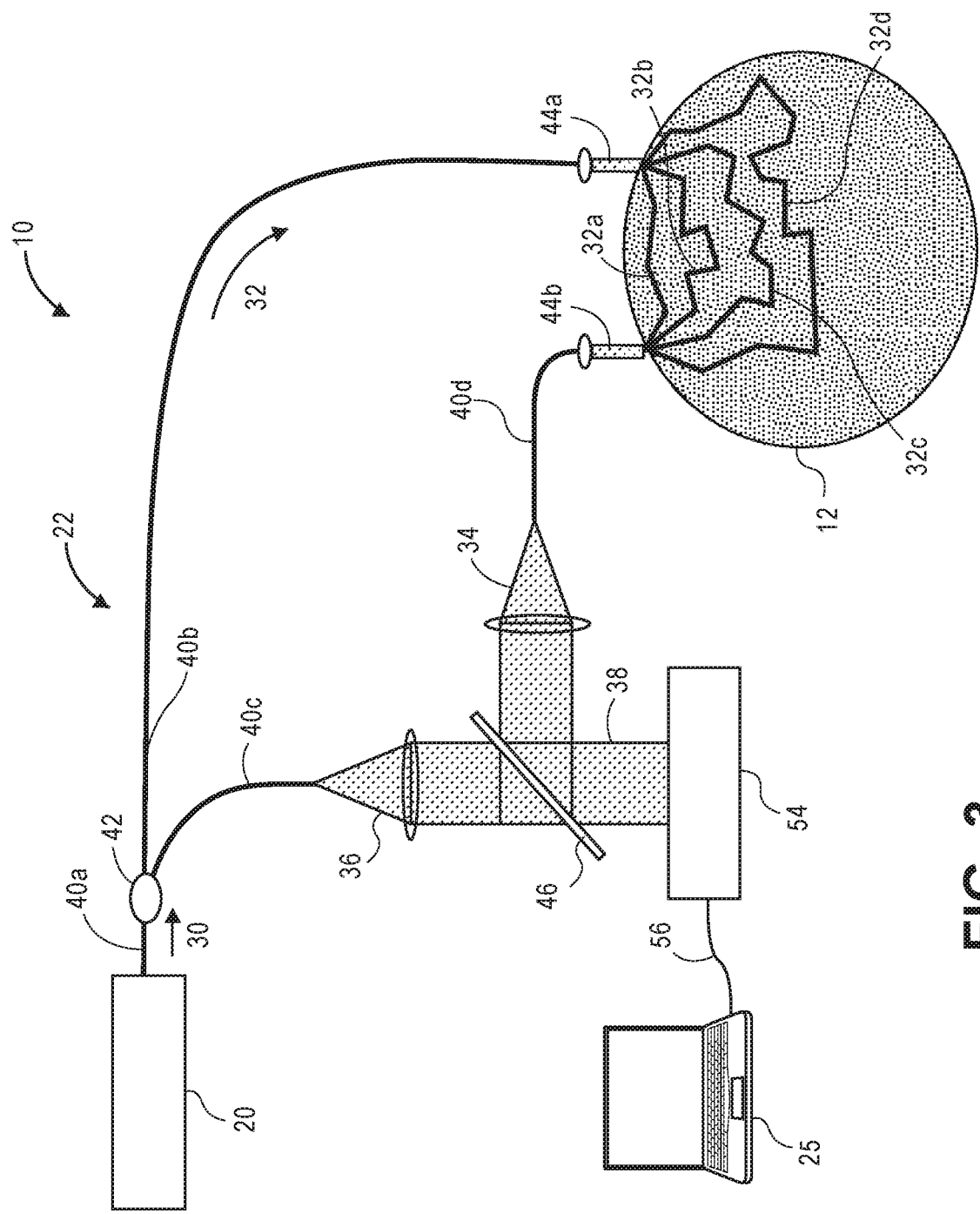
FIG. 3 is a detailed embodiment of the non-invasive optical measurement system of FIG. 1.

Referring to FIG. 3, a more detailed implementation of the non-invasive optical measurement system 10 will now be described. In this implementation, the interferometer 22 is optical fiber-based (i.e., uses optical fibers to direct light between the components), although in alternative embodiments, the interferometer 22 may direct light via free-space propagation between the components using optics, such as mirrors, as further illustrated in U.S. Provisional Patent Application Ser. No. 62/637,703, entitled "Ultrasound Modulating Optical Tomography Using Reduced Laser Pulsed Duration," U.S. patent application Ser. No. 16/266,818, entitled "Ultrasound Modulating Optical Tomography Using Reduced Laser Pulsed Duration," U.S. Provisional Patent Application Ser. No. 62/657,634, entitled "Balanced Holography Technique for Imaging in Highly Scattering Medium," U.S. patent application Ser. No. 16/299,067, entitled "Non-Invasive Optical Detection Systems and Methods in Highly Scattering Medium," U.S. Provisional Patent Application Ser. No. 62/667,770, entitled "Ultrasound-Mediated Optical Detection," and U.S. patent application Ser. No. 16/382,461, entitled "Non-Invasive Optical Detection System and Method," which are expressly incorporated herein by reference.

The interferometer 22 comprises an input optical fiber 40a that optically couples the interferometer 22 to the optical source 20 for receiving the source light 30 from the optical source 20; an optical fiber-based optical beam splitter 42 for splitting the source light 30 into the sample light 32 and the reference light 36, and a sample arm optical fiber 40b and a reference arm optical fiber 40c for respectively propagating the sample light 32 and reference light 36 along the sample arm and reference arm of the interferometer 22.

The optical beam splitter 42 may not necessarily split the source light 30 equally into the sample light 32 and reference light 36, and it may actually be more beneficial for the optical beam splitter 42 to split the source light 30 unevenly, such that the intensity of the sample light 32 is less than the intensity of the reference light 36 (e.g., 99/1 power ratio), since much of the sample light 32 will be lost after passing through the head. That is, the intensity of the sample light 32 should be boosted relative to the reference light 36 to compensate for the losses incurred by the sample light 32 as it passes through the brain 12 and the fact that only a small portion of signal light (described below) exiting the head will be detected.

The sample arm optical fiber 40b delivers the sample light 32 via an output port 44a into the brain 12, such that the sample light 32 scatters diffusively through the brain 12, and back out again, exiting the head as the neural-encoded signal light 34. As it scatters diffusively through the brain 12, various portions of the sample light 32 will take different paths through the brain 12. For purposes of brevity, only four sample light portions 32a-32d are illustrated as traveling along optical paths of different lengths (from a shallow depth to a more deeper depth), which combined into the exiting neural-encoded signal light 34, although it should be appreciated that the diffused sample light 32 will travel along many more optical paths through the brain 12. The interferometer 22 further comprises an output optical fiber 40d configured for receiving the neural-encoded signal light 34 from the brain 12 via an input port 44b.

The interferometer 22 comprises an optical beam combiner 46 configured for receiving the neural-encoded signal light 34 from the output optical fiber 44b, receiving the reference light 36 from the reference arm optical fiber 40c, and combining the neural-encoded signal light 34 and reference light 36 via superposition to generate the interference light pattern 38, which as described above has spatial components and oscillation frequency components. In the illustrated embodiment, the optical beam combiner 46 is a free-space optical beam combiner that respectively receives the neural-encoded signal light 34 and reference light 36 on different faces of the optical beam combiner 46 and outputs the interference light pattern 38 on another different face of the optical beam combiner 46.

Figure 4:
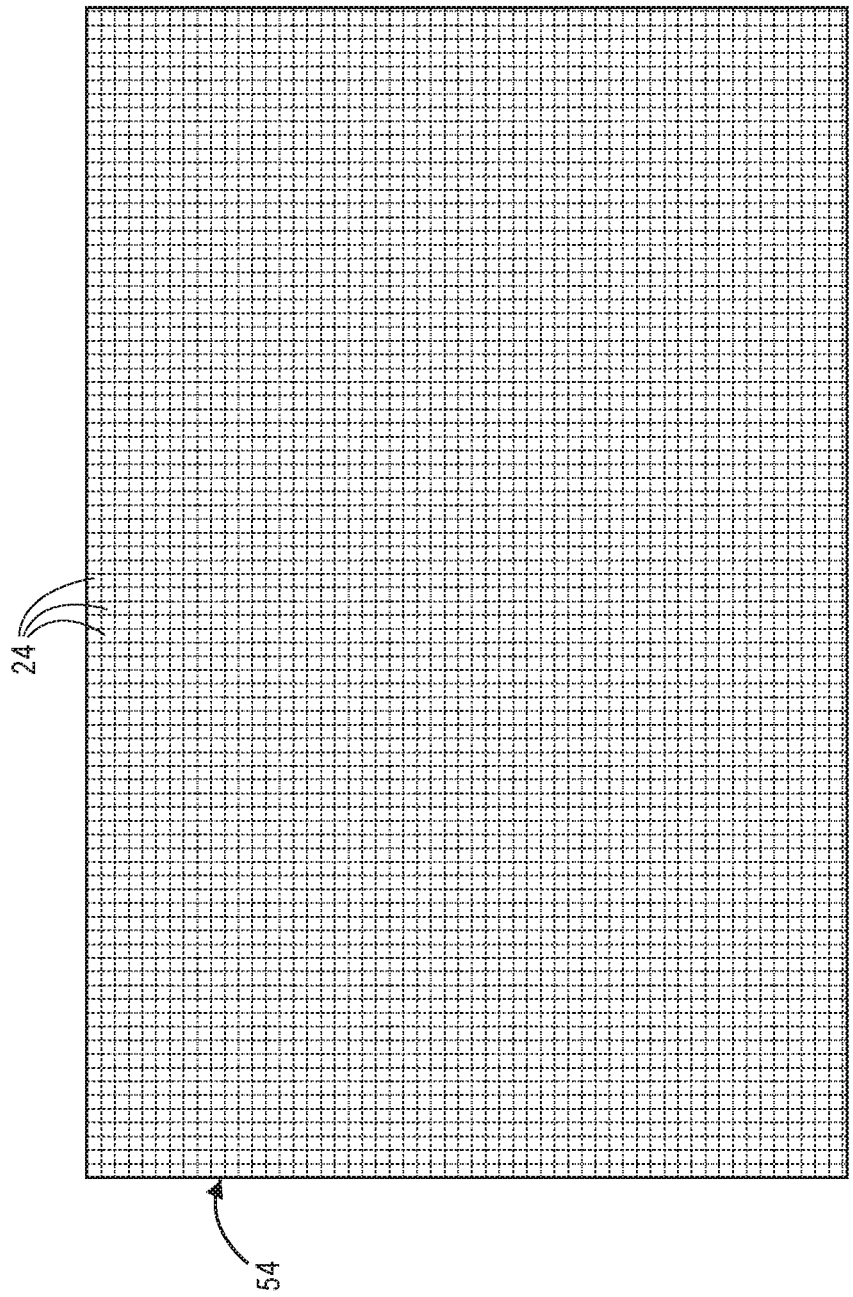
FIG. 4 is a plan view of an optical detector array used in the non-invasive optical measurement system of FIG. 3.

Referring to FIG. 4, the optical detector array 24 is configured for simultaneously detecting an array of intensity values respectively of the array of spatial components (referred to herein as spatial component intensity values or spatial component intensity value arrays) of the interference light pattern 38 during each measurement period. In the case where the interference light pattern 38 is a speckle light pattern, the spatial components are speckle grains (approximately the size of a wavelength of the light) of the speckle light pattern 38. The optical detector array 24 may be implemented as a camera 54 with a frame rate that can be controlled by the controller 26 (shown in FIG. 1) in coordination with the optical wavelength sweeps of the optical source 20 to match the measurement period.

Although not illustrated, the non-invasive optical measurement system 10 may include magnification optics and/or apertures to magnify the individual speckle grains, which may have a size on the order of the wavelength of the near-infrared or visible light used to acquire the data voxel, and hence on the order of hundreds of nanometers in size, to approximately the sizes of the individual optical detectors 24. Thus, in the illustrated embodiment, the pixel sizes and pitches of the optical detectors 24 are matched to the speckle grain sizes and pitches of the interference light pattern 38 via the appropriate magnification, although other embodiments are possible.

Significantly, the use of a large number of optical detectors 24 ultimately increases the SNR of the extracted oscillation frequency component intensities relative to a conventional iNIRS system that uses a single large detector. Notably, according to the known principles of parallel speckle detection from strongly scattering media, it is known that a single-pixel detector (as in a conventional iNIRS system) will not scale to high signal to noise ratios. In particular, the aggregate signal over a large single-pixel detector would scale as the square root of detector size, but so would shot noise in the background, and hence the signal to noise ratio performance of a large detector would not increase with detector size. In contrast, with detection at each detector (or pixel), the aggregate signal scales linearly with the number of pixels, while the aggregate background shot noise scales as the square root, and hence signal to noise performance increases as the square root of the number of pixels, giving a strong advantage for using large numbers of pixels.

Furthermore, as discussed above, some of the optical fibers 40a, 40b, 40c, and 40d, shown in FIG. 3, may advantageously be multi-mode optical fibers and/or bundles of single-mode optical fibers with matched optical path lengths, and in this case, the output optical fiber 40d is a multi-mode optical fiber or single-mode optical fiber bundle. In the case where a single detector was used in the conventional iNIRS system, a single-mode optical fiber was required, which results in the averaging of the spatial component intensity value array of the interference light pattern 38 and hence destructive interference that limits the detected signal magnitude. In contrast, the use of multi-mode optical fibers or single-mode optical fiber bundles in the interferometer 22 allows the optical detectors 24 to respectively detect the spatial component intensity value array of the interference light pattern 38, with the accompanying advantage of boosting light collection efficiency, maximizing the number of photons collected without destructive averaging, and leading to higher SNR. The sample arm optical fiber 40b may also comprise a multi-mode optical fibers and/or single-mode optical fiber bundle, whereas the input optical fiber 40a and reference arm optical fiber 40c are preferably single-mode optical fibers.

It should be noted that although the interferometer 22, for purposes of brevity, is described in FIGS. 1 and 3 as only creating one interference light pattern 38 from the neural-encoded signal light 34 and reference light 36 for each measurement period, and further describes the non-invasive optical measurement system 10 showing only one optical detector array 24 for detecting such interference light pattern 38, the interferometer 22 may create multiple interference light patterns 38 (typically phase-modulated) from the neural-encoded signal light 34 and reference light 36 for each measurement period, in which case, the non-invasive optical measurement system 10 may have an equal number of optical detector arrays 24 for detecting such interference light patterns 38. In another alternative embodiment, the interferometer 22 can be implemented in an off-axis holography configuration. In this case, the trajectory of the reference light 36 as it impinges on the optical beam combiner 46 is tilted, such that a constant phase shift introduced into adjacent spatial components of the interference light pattern 38 upon detection by the optical detector array 24. In this case, the optical detector array 24 will be effectively partitioned into two interlaced optical detector arrays that detect two phase-modulated interference light patterns 38.

In the embodiment illustrated in FIG. 3, at least a portion of the processor 28 (illustrated in FIG. 1) is implemented as a central processor unit (CPU) in the computing device 25. In one embodiment described in further detail below, the entirety of the processor 28 may be embodied in the computing device 25, and in another embodiment described in further detail below, a portion of the processor 28 is implemented in a camera 54 that also includes the optical detector array 24, while the remaining portion of the processor 28 is embodied in the computing device 25, which may be coupled to the output of the camera 54 via an electrical cable 56.

Figure 5B:
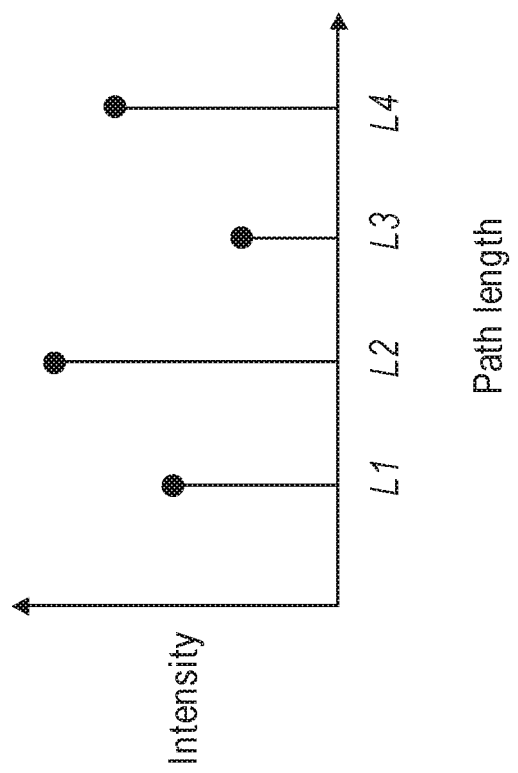
FIG. 5B is a timing diagram illustrating exemplary optical path length intensities corresponding to the exemplary oscillation frequency components of FIG. 5A.
Figure 5A:
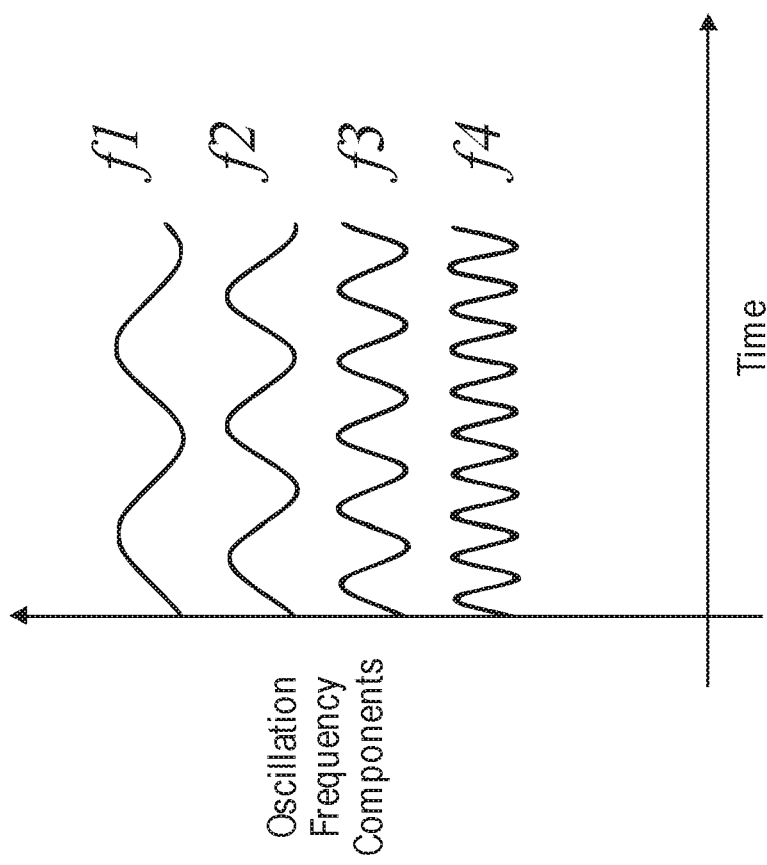
FIG. 5A is a timing diagram illustrating exemplary oscillation frequency components of an interference light pattern generated by the non-invasive optical measurement system of FIG. 3.

Significantly, the oscillation frequency components of the interference light pattern 38 are respectively encoded with different depths of the brain 12. For example, four exemplary oscillation frequency components f1-f4 (shown in FIG. 5A) respectively correspond to four exemplary intensities of the light at four different optical path lengths L1-L4 (shown in FIG. 5B) (which directly correlate to depths of the fast-optical signal within the brain 12). The processor 28 is configured for deriving an array of intensity values of each of the oscillation frequency components f1-f4 over the optical detector array 24 (referred to herein as oscillation frequency component intensity values or oscillation frequency component intensity value arrays) from the detected spatial component intensity value array of the interference light pattern 38 during at least one of the measurement periods, reducing each of the derived oscillation frequency component intensity value arrays to a single oscillation frequency component intensity value (e.g., by computing a mean of each respective oscillation frequency component intensity value array), and determining a depth of the fast-optical signal in the brain 12 (correlated to the optical path lengths L1-L4, at least partially, based on these reduced oscillation frequency component intensities values.

In one embodiment, the processor 28 determines depth of the fast-optical signal (and alternatively hemodynamic changes), and thus the neural activity, within the brain 12, e.g., by comparing the current signal intensity-frequency profile (in this case, the computed means of the derived oscillation frequency component intensity value arrays of the currently detected interference light pattern 38) with a patient-specific baseline signal intensity-frequency profile (e.g., a previously acquired signal intensity-frequency profile) (in this case, corresponding reference frequency component intensity value arrays of a previously detected interference light pattern 38).

Figure 6B:
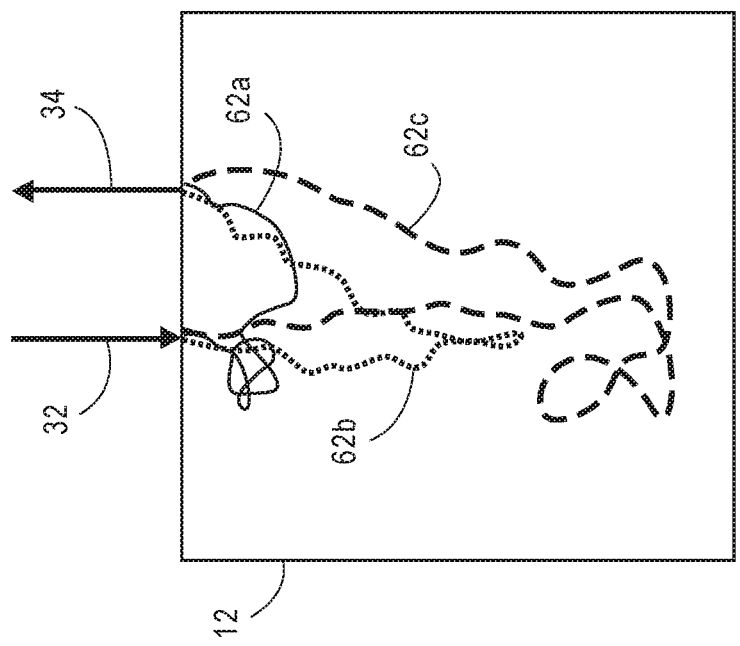
FIG. 6B is a plan view illustrating exemplary path lengths of photons corresponding to different frequency bands of the exemplary signal intensity-frequency profile of FIG. 6A.
Figure 6A:
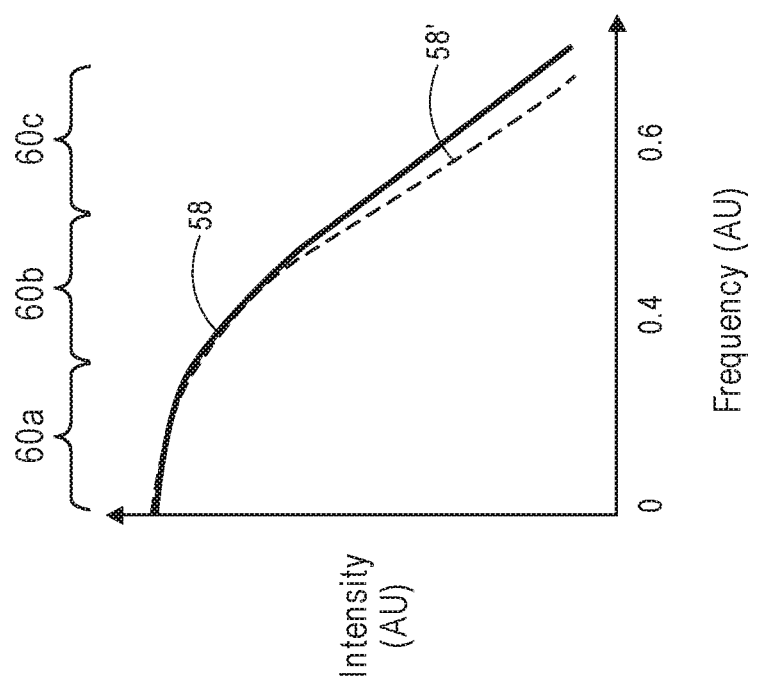
FIG. 6A is a timing diagram illustrating an exemplary signal intensity-frequency profile generated by the non-invasive optical measurement system of FIG. 3.

For example, referring to FIGS. 6A and 6B, it can be seen that there is a strong correlation between the depth of penetration of photons of the sample light 32 within the brain 12 and the shape of the signal intensity-frequency profile 58. That is, the signal intensity-frequency profile 58 can be correlated to spatial depth information (i.e., the tail end of the signal intensity-frequency profile 58 contains relatively deeper depth information, whereas the front end of the signal intensity-frequency profile 58 contains relatively shallow depth information), and thus, the spatial depth of the fast-optical signal along the bundle of detected optical path bundle 14 (shown in FIG. 1) may be determined. That is, it is known that the occurrence of the fast-optical signal along the detected optical path bundle 14 will perturb the photons of the sample light 32 at the depth of the fast-optical signal along the detected optical path bundle 14, thereby changing the intensity of the photons of the sample light 32 having an optical path length corresponding to that depth.

For example, a relatively early frequency band 60a of the signal intensity-frequency profile 58 is weighted for photons that travel a relatively short distance along the detected optical path bundle 14; that is, photons 62a that penetrate superficially into the brain 12. A relatively medial frequency band 60b of the signal intensity-frequency profile 58 is weighted for photons that travel a relatively medial distance along the detected optical path bundle 14; that is, photons 62b that penetrate further into the brain 12. A relatively high frequency band 60c of the of the signal intensity-frequency profile 58 is weighted for photons that travel a maximum distance along the detected optical path bundle 14; that is, photons 62c that penetrate even further into the brain 12.

Thus, it can be appreciated that the signal intensity-frequency profile 58 of the detected signal light 34 contains intensity-optical path length information in which the spatial depth of a fast-optical signal is encoded, and thus, a fast-optical signal that occurs at a certain depth in the brain 12 will cause a corresponding perturbation in the signal intensity-frequency profile 58. For example, as shown in FIG. 6A, there exists a perturbation between the baseline signal intensity-frequency profile 58 in the absence of a fast-optical signal, and a signal intensity-frequency profile 58' in the presence of a fast-optical signal. The fast-optical signal causes a measurable perturbation in the signal intensity-frequency profile 58 in frequency bands 60b and 60c, indicating a change in scattering or absorption in the photons in the mid-level or maximum depth in the brain 12, and thus, a fast-optical signal at this depth in the brain 12.

Auto-correlation techniques can be used to perform this comparison, such as, e.g., the auto-correlation technique described in U.S. Provisional Patent Application Ser. No. 62/692,124, entitled "Interferometric Frequency-Swept Source and Detector in a Photonic Integrated Circuit," which is expressly incorporated herein by reference.

Referring back to FIG. 2, because the neural-encoded signal light 34 comprises a collection of the scattered light of different optical path lengths that is swept through a range of optical wavelengths (by virtue of the source light 30 swept through the range of optical wavelengths), the interference light pattern 38 created by the dynamic interference between the swept neural-encoded signal light 34 and reference light 36 results in a dynamic fringe pattern 52 for each optical wavelength sweep, e.g., 50a or 50b.

As adapted from Michael A. Choma, et al., "*Sensitivity Advantage of Swept Source and Fourier Domain Optical Coherence Tomography*," Optics Express, Vol. 11, No. 18, 8 Sep. 2003), the ith optical detector 24 will output an intensity in accordance with the equation:

$$P_{Di}(k_m) = S(k_m)P_R + S(k_m)P_S + 2S(k_m)\sqrt{P_R P_S}\cos(2k_m\Delta x + \varphi_i),\quad [2]$$

where $k_m$ is the optical wavenumber (equal to $2\pi/\lambda$, where $\lambda$ is the instantaneous wavelength of the signal light 34 at sample point m, $P_{Di}(k)$ is the instantaneous power of the electrical current output by the ith detector 24 at the optical wavenumber $k_m$, $S(k_m)$ is the source spectral density (watts per wavenumber $k_m$), $\Delta x$ is the optical pathlength difference between the reference and sample arms of the interferometer 22, $P_R$ is the power on the detector from the reference light 36, $P_S$ is the power on the detector from the signal light 34, and $\varphi_i$ is the interferometric phase shift associated with the ith optical detector 24. The term inside of the cosine function represents the phase of the fringe pattern 52, and as the optical pathlength difference $\Delta x$ increases or decreases, the fringe pattern 52 oscillates, with a full period of oscillation occurring every $2\pi$ radians. The frequency at which the fringe pattern 52 oscillates for any given optical pathlength difference $\Delta x$ corresponds to the oscillation frequency component in the interference light pattern 38 correlated to that optical pathlength difference $\Delta x$.

Figure 7A:
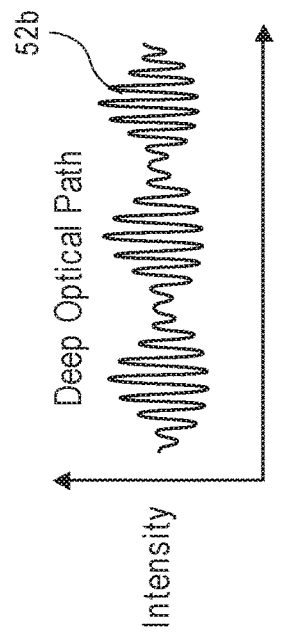
FIG. 7A is a timing diagram illustrating a fringe pattern of interference light corresponding to an optical path at a relatively shallow depth.
Figure 7B:
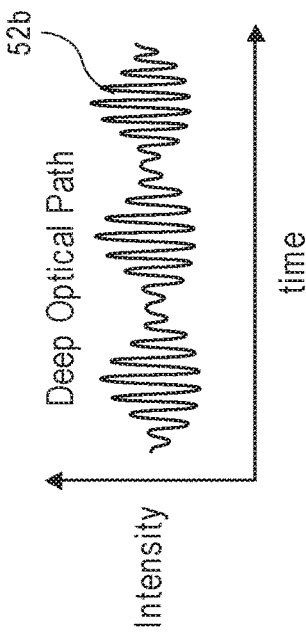
FIG. 7B is a timing diagram illustrating a fringe pattern of interference light corresponding to an optical path at a relatively deep depth.

Equation [2] shows that the oscillation frequency of the fringe pattern 52 increases with the optical pathlength difference $\Delta x$, and thus the depth of the optical path, since the optical pathlength difference $\Delta x$ serves as a multiplier term inside the cosine function that increases the total phase of the fringe pattern 52. Thus, relatively shallow optical path will yield, over a series of sweeps, a series of fringe patterns 52a with a relatively slow oscillation frequency (see FIG. 7A), whereas a relatively deep optical path will yield, over a series of sweeps, a series of fringe patterns 52b with a relatively fast oscillation frequency (see FIG. 7B).

The oscillation frequencies of the fringe pattern 52, as observed in time on the detector array 24, are ultimately dictated by the respective elapsed times of each detected sample relative to the start time of the optical wavelength sweep 50. In particular, at any moment in time, the optical wavenumber k is given by: $[3] k_0 = t(\Delta k/\Delta t)$, where t is time, $k_0$ is the starting wavenumber, and $\Delta t$ is the total time of the optical wavelength sweep (in this case, equal to the measurement period z in equation [1]) and $\Delta k$ is the total optical bandwidth through which the narrowband optical source of linewidth $\Lambda$ is swept. The swept source light 30 ideally has values at M evenly spaced wavenumbers $K=\{k_1, k_2, \ldots, k_M\}$ with wavenumber spacing $\delta k = \Delta k/M$, $\delta k$ having a lower limit determined by the linewidth $\Lambda$. Each wavenumber spacing takes a time $\delta t = \Delta t/M$, and thus, the optical wavelength sweep 50 can be represented as a time series with an N number of time points, each lasting $\delta t$ over a total time duration $\Delta t$. Thus, the periods of the oscillations of the fringe pattern 52 can be given as: $[4] f = \sum_{m=1} \delta t * m$. The maximum detectable oscillation frequency of the fringe pattern 52 is on the order of $$\frac{1}{\delta t},$$

whereas the minimum detectable oscillation frequency of the fringe pattern 52 is on the order of $$\frac{1}{\Delta t}.$$

For example, if the total time $\Delta t$ of the optical wavelength sweep 50 is 10ρs, and the total number of steps M is 1000, resulting in a time $\delta t$ for each step of 10 ns, the maximum oscillation frequency of the fringe pattern 52 would be 1/10 ns=100 MHz, while the minimum oscillation frequency of the fringe pattern 52 would be 1/10ρs=100 KHz.

The intensity of fringe pattern 52 at each oscillation frequency for any particular optical detector 24 can be determined from the spatial component intensity value of the interference light pattern 28 sampled by that optical detector 24. In particular, based on equation [2], the sampled signal from the ith optical detector 24 is:

$$D_i[k_m] = \frac{\rho}{2}S[k]\left(P_R + P_S + 2\sqrt{P_R P_S}\cos(2k_m\Delta x + \varphi_i)\right),\quad [5]$$

where $m \in \{1, M\}$, $\rho$ is the detector responsivity, and $S[k_m]$ is the sample illumination power $\frac{1}{4}\Lambda S(k_m)$ach oscillation frequency component intensity value for the ith optical detector 24 can be determined by discrete Fourier transforming equation [5] to yields a depth profile:

$$D_i[x_n] = \sum_{m=1}^{M} D_i[k_m] * e^{-j2k_m x_n}$$ [6]

Thus, it can be appreciated from equation [6] that the sampled intensity of the interference light pattern 38, and with respect to a single optical detector 24, the sampled spatial component intensity values of such interference light pattern 38, over the optical wavelength sweep 50 (i.e., during the measurement period τ) contains oscillation frequency components, each of which is associated with an optical path difference between the sample arm and reference arm that is directly correlated to a depth within the brain 12.

As briefly discussed above, the processor 28 may derive each of the oscillation frequency component intensity value arrays over the optical detector array 24 from the spatial component intensity value array of the interference light pattern 38, after which the processor 28 computes the mean of each oscillation frequency component intensity value arrays to obtain single oscillation frequency component intensity values, and thus, the magnitudes of the neural-encoded signal light 34 at the respective optical path lengths corresponding to the single oscillation frequency component intensity values, which yields a signal intensity-frequency profile. Referring back to FIG. 1, two techniques for accomplishing this will now be described.

In one embodiment, the processor 28 of the non-invasive optical measurement system 10 is configured for deriving the oscillation frequency component intensity value arrays over the optical detector array 24 from the spatial component intensity value array of the interference light pattern 38 during a single measurement period by computing a Fourier transform of the spatial component intensity value array of the interference light pattern 38. In this case, the processor 28 may employ equation [6] for an ith optical detector 24, with the depth being represented by $x_n$, each oscillation frequency component intensity value being represented by $D_i[x_n]$, and each spatial component intensity value of the interference light pattern 38 detected at an optical wave number $k_m$ of the optical wavelength sweep being represented by $D_i[k_m]$.

Figure 8A:
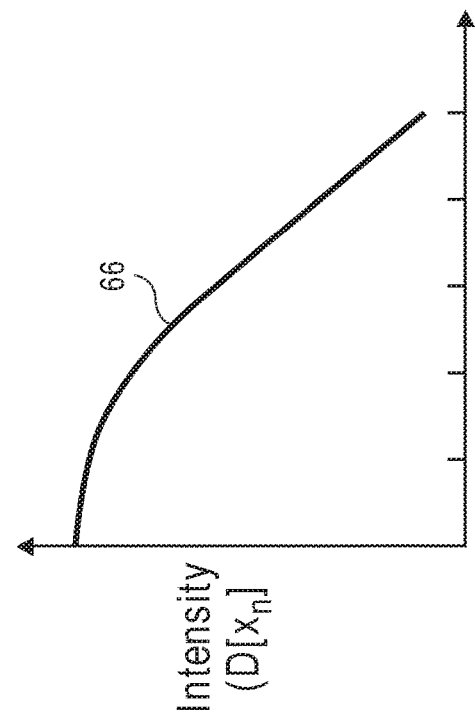
FIG. 8A is a diagram illustrating an exemplary time-of-flight (TOF) profile detected by an optical detector of the non-invasive optical measurement system of FIG. 3.
Figure 8B:
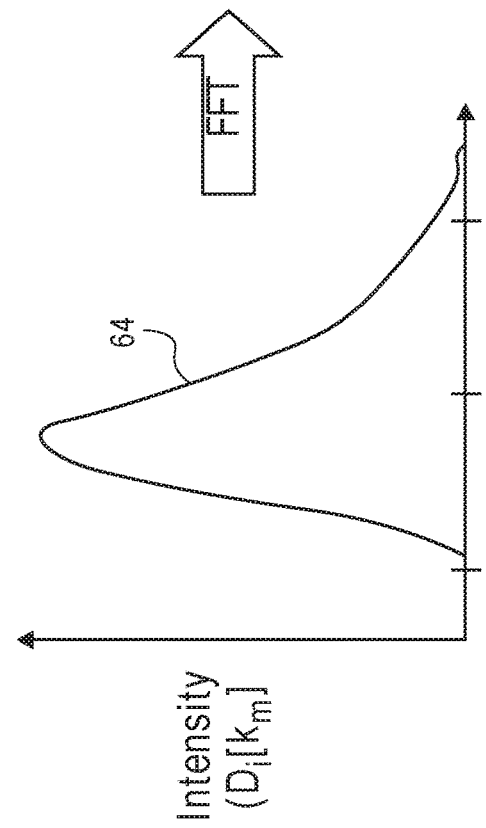
FIG. 8B is a diagram illustrating an exemplary signal intensity-frequency profile transformed from the TOF profile of FIG. 8A.

Over the entire measurement period, spatial component intensity values of the interference light pattern 38 detected by the ith optical detector 24 $D_i[k_m]$ over a period of time can be represented by the time-of-flight (TOF) profile 64 exemplified in FIG. 8A, whereas the oscillation frequency component intensity values (i.e., the depth in the brain 12) $D_i[x_n]$ derived in accordance with equation [6] can be represented by the intensity-frequency profile 66 exemplified in FIG. 8B.

For this particular embodiment, the camera 54 (shown in FIG. 3) containing the optical detector array 24 may be conventional, such as a charge coupled device (CCD) or a CMOS detector array, and comprises an array of pixels corresponding to the array of optical detectors 24, which continuously samples the spatial component intensity value array $D_i[k_m]$ of the interference light pattern 28 at a set frequency (or frame rate) over the full range of optical wavenumbers $k_m$ of the optical wavelength sweep 50a or 50b (shown in FIG. 2).

In this case, the output of the CCD camera may be an M number of spatial component intensity value arrays combined as a data cube (i.e., equal to the number of optical wavenumbers $k_m$), with each spatial component intensity value array containing intensity values $D_i[k_m]$ for all of the optical detectors 24. The processor 28, the entirety of which can be embodied in the computing device 25 (shown in FIG. 3), such as that found in a general purpose computer, may be further configured for computing the Fourier transform of the array of spatial component value intensity values $D_i[k_m]$ over the optical detector array 24 in accordance with equation [6] to obtain the oscillation frequency component intensity value arrays $D[x_n]$, computing the mean of each oscillation frequency component intensity value array $D[x_n]$ over the optical detector array 24 to obtain a single oscillation frequency component value for each oscillation frequency component, and if necessary, performing post-processing, such as determining the location of neural activity in the brain 12, as described above. It should be appreciated that this embodiment requires the frame rate of the camera 54 to be at least as fast as the highest oscillation frequency component of interest (which correlates to the wavenumber spacing δt, and coincidentally, the greatest depth of the brain 12).

In another particularly advantageous embodiment, the processor 28 of the non-invasive optical measurement system 10 is configured for deriving the oscillation frequency component intensity values arrays over the optical detector array 24 from the spatial component intensity value array of the interference light pattern 38 during a plurality of measurement periods. The processor 28 accomplishes this by, for each optical detector 24, locking in the different oscillation frequency components respectively during the plurality of measurement periods (i.e., the processor 28 locks in a first oscillation frequency component during a first measurement period, locks into a second different oscillation frequency component during a second measurement period, locks into a third different oscillation frequency component during a third measurement period, and so on until all of the oscillation frequency components have been detected).

In this case, the processor 28 does not employ equation [6] to compute Fourier transforms $D[x_n]$ of the array of intensity values $D_i[k_m]$ detected at the optical wave number $k_m$ of the optical wavelength sweep. Rather, since the processor 28 locks in each oscillation frequency component one at a time, the sampled spatial component intensity value array of the interference light pattern 38 is exclusively associated with that lock-in oscillation frequency component, and therefore, the spatial component intensity value array is representative of the oscillation frequency component intensity value array, and as such, the processor 28 can directly measure the intensity values of each oscillation frequency component. It should be appreciated that, while it is preferred that the processor 28 sequentially lock in the oscillation frequency components in an incremental order (e.g., from low to high or from high to low), the processor 28 may lock in the oscillation frequency components in any order.

For this particular embodiment, the camera 54 (shown in FIG. 3) containing the optical detector array 24 may be a lock-in camera that locks into each oscillation frequency component and acquires the corresponding oscillation frequency component intensity value array over the optical detector array 24, with the computing device 25 computing the mean of each oscillation frequency component intensity value array over the optical detector array 24 to obtain a single oscillation frequency component value for each oscillation frequency component, and if necessary, performing post-processing, such as determining the location of neural activity in the brain 12, as described above.

In general, lock-in cameras include a class of digital cameras in which multiple measurements of a light field are rapidly made at each pixel in a temporally precise fashion synchronized with an external trigger or oscillation and stored in multiple "bins" within each pixel, in contrast with conventional cameras, which store only one value per pixel that merely aggregate the incoming photo-electrons over the camera frame integration time. Lock-in cameras may also perform on-chip computations on the binned values (e.g., using an on-chip field-programmable gate array (FPGA), enabling a portion of the processor 28 to be embodied in the lock-in camera. Lock-in cameras perform analog lock-in detection while outputting only the information, such as oscillation amplitude and phase shift, on the AC signal component at the temporal frequency to which it is locked. Since the information output by the lock-in camera is only the amplitude or phase shift parameters of a given frequency component, lock-in cameras dramatically increase the bit efficiency of analog to digital conversion by using all the bits to represent only the AC signal of interest. Lock-in cameras also reduce the amount of data to be transferred by transmitting only one frame of the measurement, instead of multiple frames of raw images composed of both the AC signal of interest and background, which may be later digitally processed to extract amplitudes and phases of particular frequency components.

Thus, the key feature of lock-in cameras is their ability to rapidly capture and store multiple sequential samples of the light field, with sample-to-sample latencies shorter than readout times of conventional cameras. This feature enables them, for example, to sample a modulated light field at the same frequency as the modulation, such that subtraction across successive samples, or other operations, such as quadrature detection (discussed below) will extract the component of the signal that is modulated at the modulation frequency, while subtracting off the unmodulated ("DC") background or other background at other frequencies. Similarly, lock-in cameras can be used to make a series of such measurements or comparisons, locked to an external trigger signal (generated by the controller 26), rapidly in order to extract such modulated components from a rapidly changing light field arising from a dynamic, disordered biological specimen.

Figure 9:
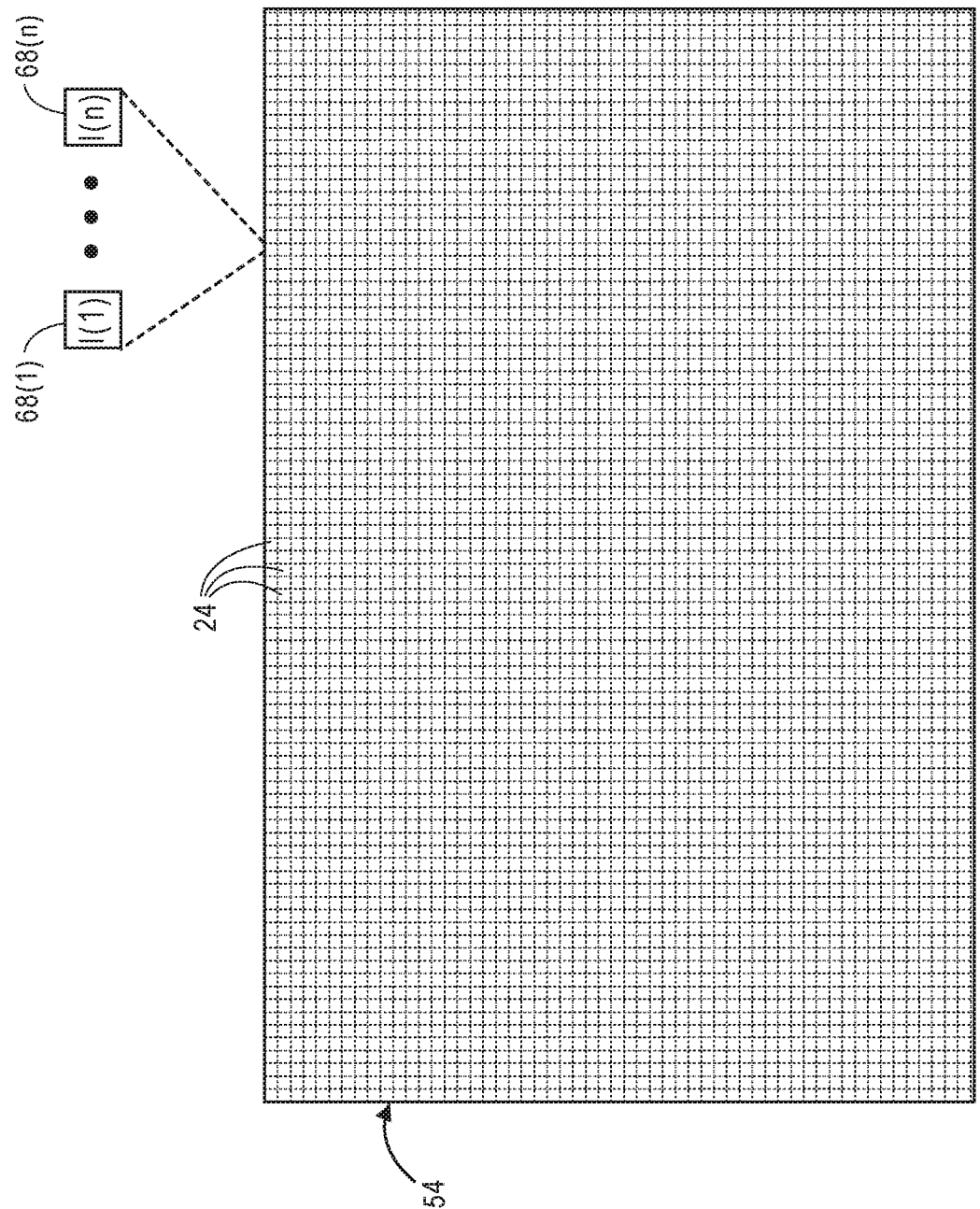
FIG. 9 is a plan view of a lock-in camera used by the non-invasive optical measurement system of FIG. 3.

Thus, as illustrated in FIG. 9, each pixel 24 of the lock-in camera 54 comprises a plurality of bins 68(1)-68(n) in which an n number of detected intensity values I(1)-I(n) of the corresponding spatial component of the interference light pattern 38 sampled during each cycle of a particular oscillation frequency component is accumulated in a manner that allows the lock-in camera 54 to lock in that particular oscillation frequency component. The lock-in camera 54 routes the sampled intensity values I to the different bins 68 at a frequency determined by its modulation frequency. In the illustrated embodiment, such lock-in technique comprises accumulating at least two sequential instances of the n number of intensity values I detected during each cycle of the respective oscillation frequency component respectively in at least two bins 68 (bin 1 and bin 2), and performing a function on the accumulated contents of the entire bins 68.

That is, for one cycle of an oscillation frequency component, the first intensity value I(1) sampled during that cycle will be added to bin 68(1), the second intensity value I(2) sampled during that cycle will be added to bin 68(2), and so forth until an n number of intensity values I sampled during that cycle have been respectively added to the n number of bins. For the next cycle of the same oscillation frequency component, the first intensity value I(1) sampled during this next cycle will be added to bin 68(1), the second intensity value I(2) sampled during this next cycle will be added to bin 68(2), and so forth until of n number of intensity values I sampled during that cycle have been respectively added to the 68(n) number of bins. This binning process will be repeated until the oscillation frequency component has been completely cycled through the measurement period (i.e., the frame rate of the lock-in camera 54), accumulating the digitized intensity values I in each of the respective bins 68. The lock-in camera 54 may have an analog-to-digital converter (ADC) (not shown) that digitizes the intensity values I of each spatial component of the interference light pattern 38 over the cycle of the oscillation frequency component, and one or more switches (not shown) that directs the digitized intensity values I into each of the bins 68 over the cycle of the oscillation frequency component.

Significantly, the n number of intensity values I are sampled in accordance with a consistent time pattern relative to the desired oscillation frequency component to be locked into, such that sampling always occurs at predetermined phases of this oscillation frequency component over the measurement period.

Figure 10A:
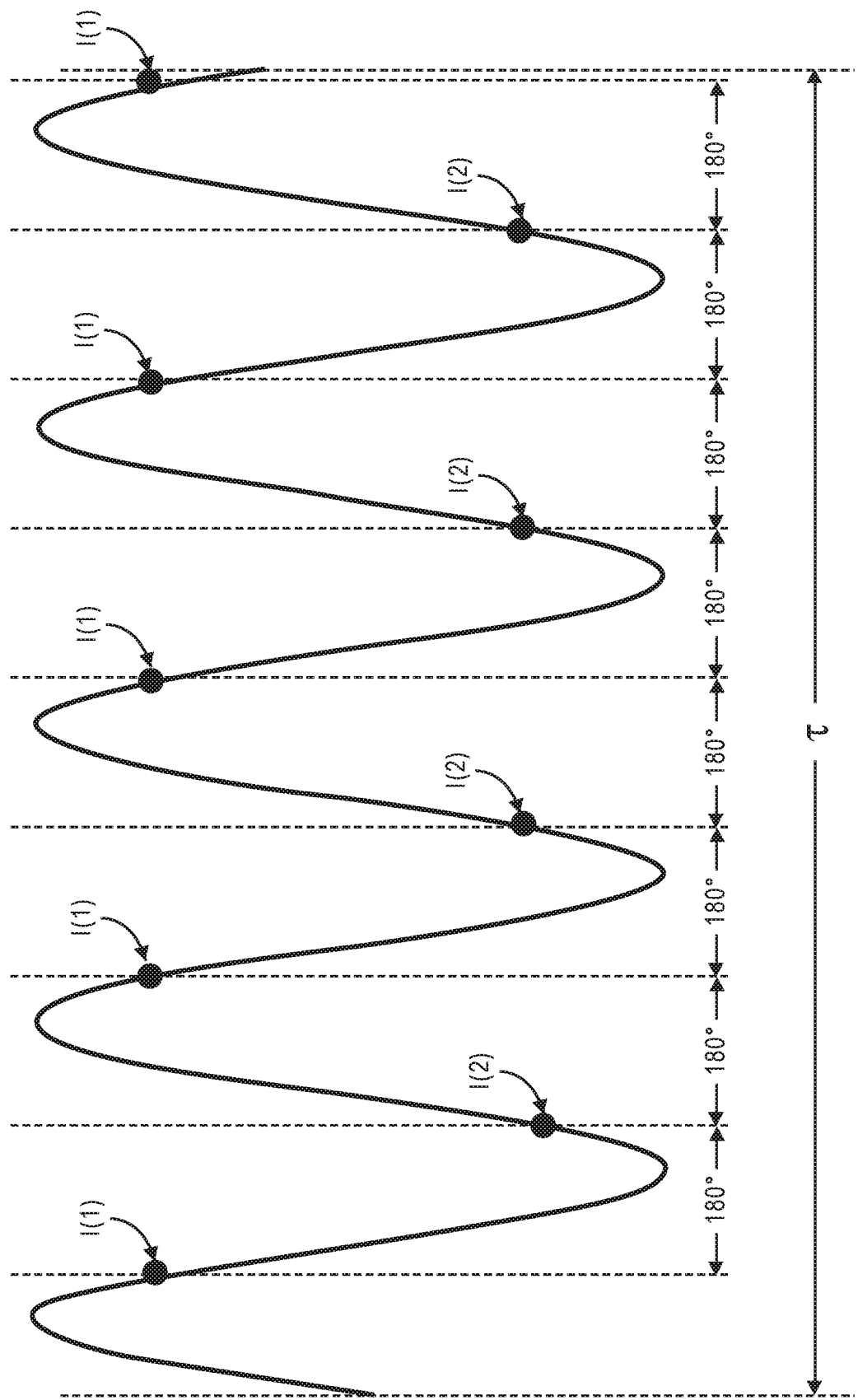
FIG. 10A is a timing diagram illustrating one method used by the lock-in camera of FIG. 9 to lock in an oscillation frequency component.

For example, if n=2 (i.e., a two-bin arrangement), the time period between the two sequential sampled intensity values I(1) and I(2) may be selected to equal a 180-degree phase difference in the oscillation frequency component to be locked in, as illustrated in FIG. 10A. In this case, the first digitized intensity value I(1) will be added to bin 1, the second digitized intensity value I(2) will be added to bin 2, the third digitized intensity value I(1) will be added to bin 1, the fourth digitized intensity value I(2) will be added to bin 2, and so forth for the duration of the measurement period $\tau$.

As another example, if n=4 (i.e., a four-bin arrangement), the time period between the two sequential digitized intensity values I may be selected to equal a 90-degree phase difference in the oscillation frequency component to be locked in, as illustrated in FIG. 10B. In this case, the first digitized intensity value I(1) will be added to bin 1, the second digitized intensity value I(2) will be added to bin 2, the third digitized intensity value I(3) will be added to bin 3, the fourth digitized intensity value I(4) will be added to bin 4, the fifth digitized intensity value I(1) will be added to bin 1, the sixth digitized intensity value I(2) will be added to bin 2, the seventh digitized intensity value I(3) will be added to bin 3, the eighth digitized intensity value I(4) will be added to bin 4, and so forth for the duration of the measurement period $\tau$.

It should be noted that the 4-bin arrangement guarantees that each of the four digitized intensity values I precisely reflects the true oscillation frequency component, and is therefore a very robust technique for extracting the oscillation frequency component from the interference light pattern 38, whereas the two digitized intensity values I in the 2-bin arrangement may not precisely reflect the true oscillation frequency component. That is, optimally, the digitized intensity values I added to bin 1 represent the 90-degree phase (peak) of the oscillation frequency component, and the digitized intensity values I added to bin 2 represent the 270-degree phase (valley) of the oscillation frequency component in bin 2, thereby maximizing the computed difference between the two bins However, there is no guarantee that bins 1 and 2 will respectively represent the peak and valley of the oscillation frequency component (as illustrated in FIG. 10A), and therefore, there may be a need to measure a large amount of these random phase events in the 2-bin arrangement, e.g., using a large number of pixels, to yield a statistical stable measurement, as discussed in further detail below.

It should also be appreciated that the Q factor of the lock-in camera 54 (which is the ratio between the central frequency and the detection bandwidth, and corresponds to the ability of the lock-in camera to resolve frequencies) decreases as the oscillation frequency to which the lock-in camera is locked deceases. Furthermore, as the oscillation frequency decreases, thereby covering fewer cycles, the detection bandwidth becomes larger, leading to a lower Q factor. That is, at the lower end of the oscillation frequencies of the interference light pattern 38, there will not be many cycles per measurement period z (or frame rate of the lock-in camera), the upper range of which is limited by the speckle decorrelation time. For example, if the speckle decorrelation time is 10 microseconds to which the measurement period z is set, the lowest accessible oscillation frequency component of the interference light pattern 38 will have a period of 10 microseconds, which corresponds to a frequency of 100 KHz. Any oscillation frequencies of the interference light pattern 38 that are so slow that they do not finish a full period within 10 microseconds are not accessible. However, a 100 KHz or lower oscillation frequency will correspond to a very short path length that represents light that has not reached the brain 12, and is therefore, not of interest. Thus, the oscillation frequency components that are of interest (i.e., the higher oscillation frequency components) are, advantageously, associated with higher Q factors, whereas the oscillation frequency components associated with the lower Q factors are not of interest.

After the lock-in camera 54 accumulates the digitized intensity values I for each pixel for each oscillation frequency component (one for each optical path length of interest within the sample, the on-board chip of the lock-in camera 54 processes the arrays of intensity values I (i.e., two cumulative intensity value arrays in the case of a two-bin arrangement, and four cumulative intensity value arrays in the case of a four-bin arrangement). As the on-board chip receives the cumulative intensity value arrays for each oscillation frequency component, it extracts this oscillation frequency component from the interference light pattern 38 on a pixel-by-pixel basis by computing a function of the cumulative intensity value arrays, resulting in a single array of intensity values for the respective pixels of the lock-in camera 54.

For example, in a two-bin arrangement, the function can be a computation of the difference between the cumulative intensity value arrays, resulting in a single array of intensity values. The contribution of the photons from the desired oscillation frequency component to the computed difference between the accumulated intensity values is much greater than the contribution of photons from other oscillation frequency components, and thus, represents the intensity of the oscillation frequency component in the interference light pattern 38. As another example, in a four-bin arrangement, the function can be a computation of a quadrature of the accumulated intensity values of the four bins 58, resulting in a single array of intensity values.

After extracting each oscillation frequency component from the interference light pattern 38, the lock-in camera 54 outputs the single array of intensity values (representing the amplitude of the locked oscillation frequency component of the interference light pattern 38) to the processor 28, which is configured for reducing the single array of intensity values for that oscillation frequency component over the array of pixels 24 to a single frequency component intensity value (e.g., by computing a mean of the single array of intensity values for that oscillation frequency component over the array of pixels 24), which indicates the magnitude of the oscillation frequency component extracted from the interference light pattern 38, and thus, the magnitude of the neural-encoded signal light 34 at the optical path length corresponding to that extracted oscillation frequency component. This process of aggregating over pixels without destructive interference is what allows the increase in signal to noise ratio over the use of a single monolithic detector, suppressing shot noise at a level 1/Sqrt[N] where N is the number of pixels combined in this way.

Notably, although the non-invasive optical measurement system 10, in this particular embodiment, measures the oscillation frequency components in the interference light pattern 38 one at a time, and thus, relative to a conventional iNIRS system, system 10 is theoretically slower to measure the magnitude of the neural-encoded signal light 34 over a large optical path length range corresponding to the oscillation frequency components, the data throughput of system 10 is actually increased, because the increased number of pixels 24 allows sufficient photons for detection of signals within the sample to be collected in a much shorter duration of time. Whereas a conventional single-pixel iNIRS system would need to average over many sweeps to collect enough photons for signal detection, e.g., neural signal detection, the total number of sweeps needed for system 10 to detect a neural signal is smaller, because of this increased signal to noise ratio, notwithstanding the need for many sequential sweeps to collect the multiple path lengths required for path length resolved detection.

The use of a large number of pixels ultimately increases the SNR of the extracted oscillation frequency component intensities relative to a conventional iNIRS system that uses a single large detector. Notably, according to the known principles of parallel speckle detection from strongly scattering media, it is known that a single-pixel detector (as in a conventional iNIRS system) will not scale to high signal to noise ratios. In particular, the aggregate signal over a large single-pixel detector would scale as the square root of detector size, but so would shot noise in the background, and hence the signal to noise ratio performance of a large detector would not increase with detector size. In contrast, with lock-in detection at each detector 24 (or pixel), the aggregate signal scales linearly with the number of pixels, while the aggregate background shot noise scales as the square root, and hence signal to noise performance increases as the square root of the number of pixels, giving a strong advantage for using large numbers of pixels.

The use of a lock-in camera, relative to a conventional camera, such as a CCD camera, also improves the SNR of the extracted oscillation frequency component intensities, since lock-in detection allows high frequency signals (e.g., 50 MHz) to be measured with a narrow band (e.g., <1 KHz). In another words, the Q factor is much higher than that of conventional detection systems, and thus, provides a higher SNR. Furthermore, the frame rate of the camera (in this case a lock-in camera) does not have to be as fast as a conventional camera to perform direct detection of the full data cube (e.g., 1 Mega pixels at a frame rate of 50 MHz) in each sweep, since it is acquiring the oscillation frequency components over several measurement periods z (i.e., only one oscillation frequency component needs to be detected and extracted during the speckle decorrelation time). As such, this particular embodiment may utilize a camera with a very large number of pixels, which may be limited when using conventional cameras that must have frame rates commensurate with the highest oscillation frequency component. In addition, a lock-in camera can filter out DC signal before digitization, and therefore provide a much higher bit efficiency, especially for the iNIRS method, where the signals contain a very large DC component due to the use of the reference beam.

Ultimately, the embodiment of the non-invasive optical measurement system 10 that measures the oscillation frequency components in the interference light pattern 38 one at a time using a lock-in camera is particularly useful in a low photon budget regime (i.e., when a relatively low number of photons are detected), which is often the case in the context of detecting tissue optical measurements at deeper depths and/or optical measurements of small neural signals with weak contrast.

Figure 11:
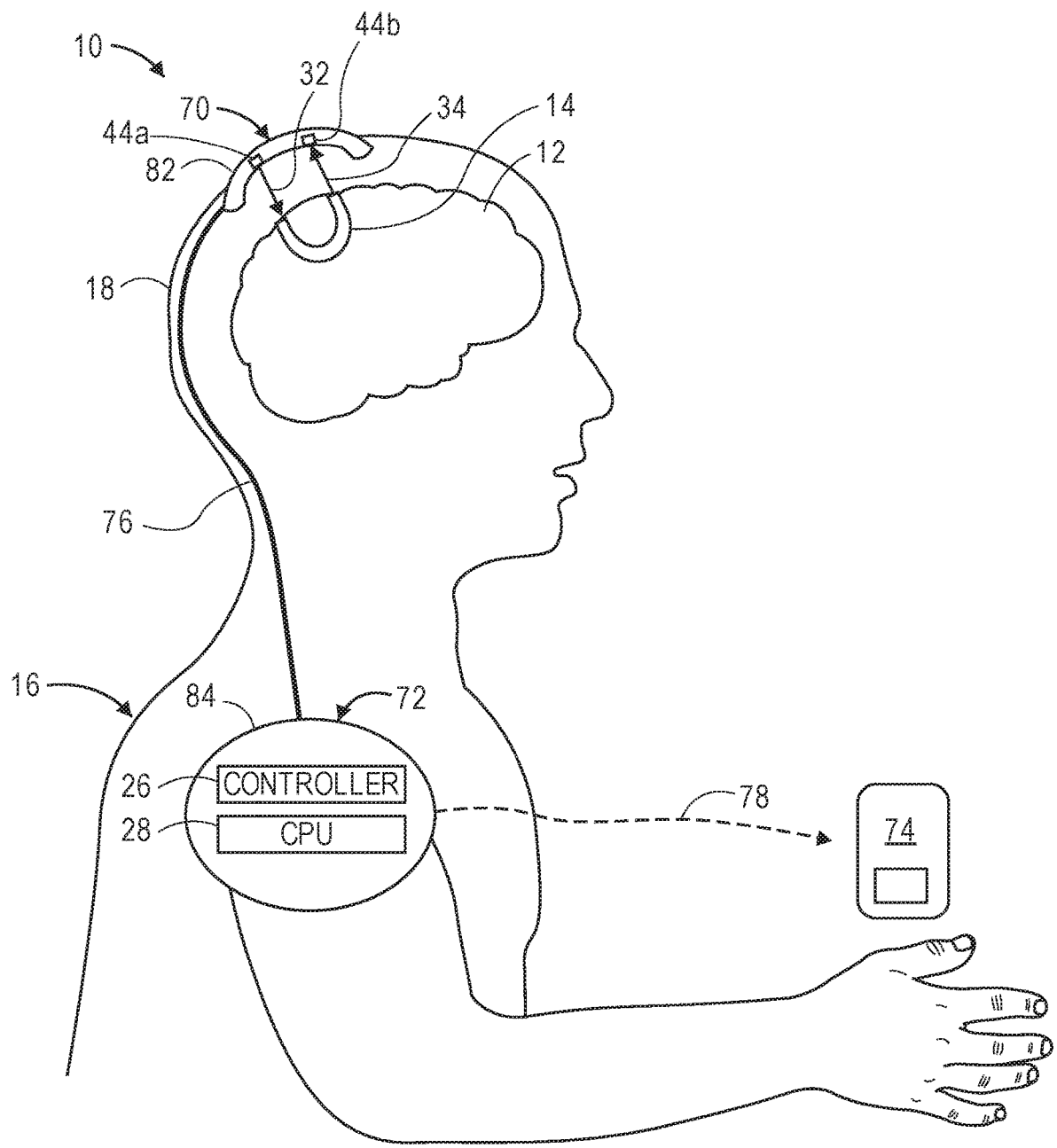
FIG. 11 is a plan view of physical implementation of the non-invasive optical measurement system of FIG. 1.

Referring now to FIG. 11, the physical implementation of the non-invasive optical measurement system 10 for use in localizing a fast-optical signal in the brain 12 of a user 16 will be described. The non-invasive optical measurement system 10 includes a wearable unit 70 that is configured for being applied to the user 16, and in this case, worn on the head 18 of the user 16; an auxiliary head-worn or non-head-worn unit 72 (e.g., worn on the neck, shoulders, chest, or arm) coupled to the wearable unit 70 via a wired connection 76 (e.g., electrical wires); and an optional remote processor 74 in communication with the patient-wearable auxiliary unit 72 coupled via a wired connection 78 (e.g., electrical wires). Alternatively, the non-invasive optical measurement system 10 may use a non-wired connection (e.g., wireless radio frequency (RF) signals (e.g., Bluetooth, Wifi, cellular, etc.) or optical links (e.g., fiber optic or infrared (IR)) for providing power to or communicating between the respective wearable unit 70 and the auxiliary unit 72, and/or a wired connection between the auxiliary unit 72 and the remote processor 74.

The wearable unit 70 comprises the optical source 20, interferometer 22, optical detector array 24, and any analog portion of the processor 28, the output port 44*a* for emitting the sample light 32 generated by the optical source 20 into the head 18 of the user 16, the input port 44*b* configured for receiving the neural-encoded signal light 34 from the head 18 of the user 16 and delivering it to the optical detector array 24 (illustrated in FIGS. 1 and 3), and a support structure 82 containing the optical source 20, interferometer 22, optical detector array 24, analog portion of the processor 28, and ports 44*a* and 44*b*.

The auxiliary unit 72 comprises the controller 26 and the digital portion of the processor 28 (illustrated in FIG. 1). The auxiliary unit 72 further comprises a housing 84 containing the controller 26 and processor 28. The controller 26 is configured for controlling the operational functions of the wearable unit 70, whereas the processor 28 is configured for processing the neural-encoded signal light 34 acquired by the wearable unit 70 to localize the fast-optical signal within the brain 12.

Figure 12:
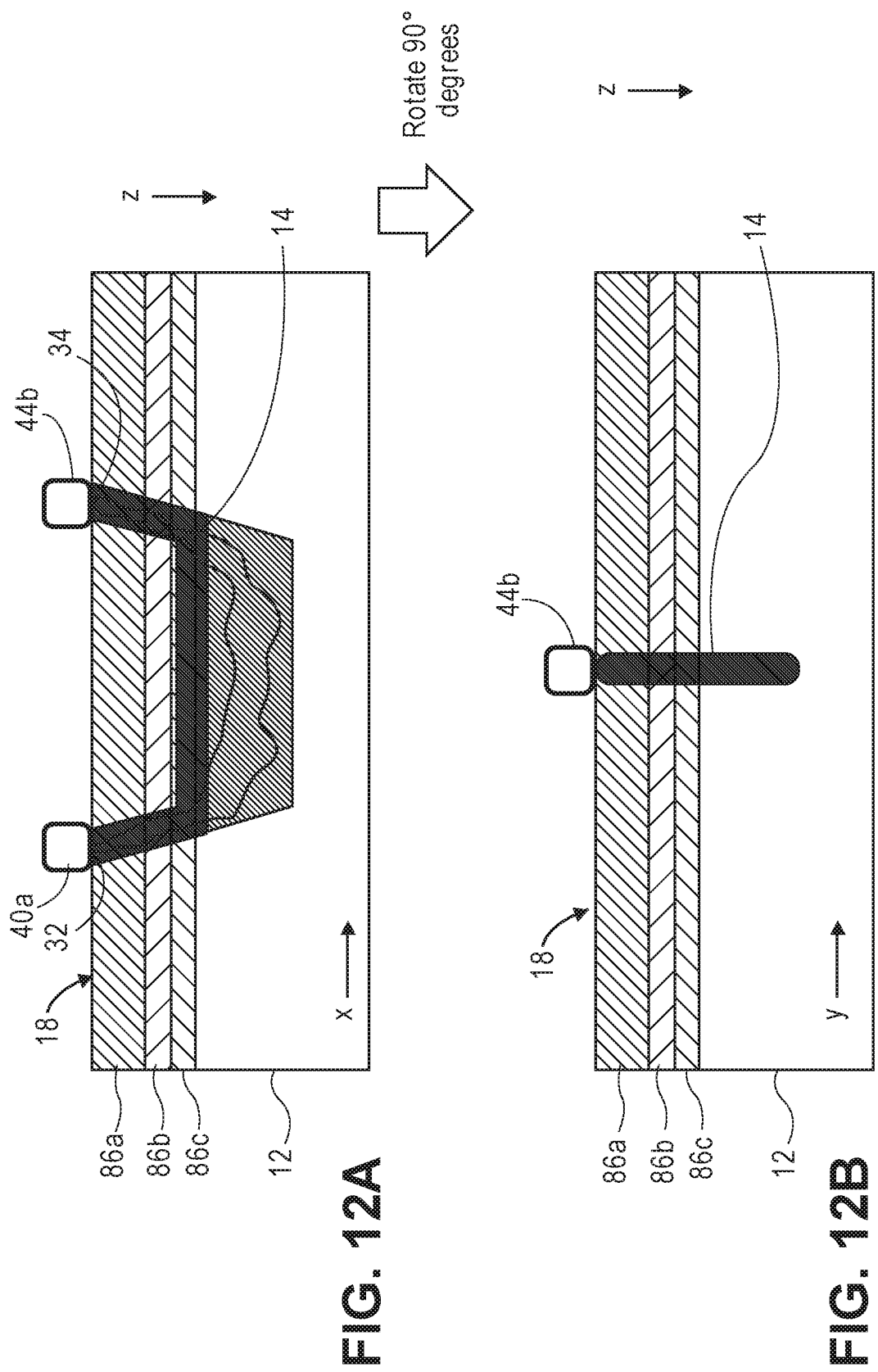
FIG. 12A is one profile view of one arrangement of the output port and input port of the wearable unit of FIG. 11, particularly illustrating the creation of a sample path in the head between the ports.
FIG. 12B is another profile view of the arrangement of the output port and input port of the wearable unit of FIG. 11.

As better illustrated in FIGS. 12A and 12B, the wearable unit 70 is configured for being placed adjacent to the head 18 of the user 16 and emitting the sample light 32 into the brain 12, where is scatters, resulting in the neural-encoded signal light 34 that exits the brain 12. In particular, the sample light 32 first passes through the scalp 86*a*, skull 86*b*, and cerebral spinal fluid (CSF) 86*c* along a relatively straight path, enters the brain 12, then exits in reverse fashion along a relatively straight path through the CSF 86*c*, skull 86*b*, and scalp 86*a*, thereby defining a banana-shaped optical path bundle 14. The wearable unit 70 may alternatively, by adding additional optical source-detector pairs, create multiple spatially separated detected optical path bundles 14 along which the light may propagate to enable x-y spatial localization of the fast-optical signal.

Referring back to FIG. 11, the support structure 82 may be shaped, e.g., have a banana, headband, cap, helmet, beanie, other hat shape, or other shape adjustable and conformable to the user's head 18, such that the ports 44*a* and 44*b* are in close contact with the outer skin of the head 18, and in this case, the scalp 86*a* of the user 16. In an alternative embodiment, optical fibers (not shown) may be respectively extended from the ports 44*a*, 44*b*, thereby freeing up the requirement that the ports 44*a*, 44*b* be disposed in close proximity to the surface of the head 18. In any event, an index matching fluid may be used to reduce reflection of the light generated by the wearable unit 70 from the outer skin of the user's scalp. An adhesive or belt (not shown) can be used to secure the support structure 82 to the head 18 of the user 16.

Figure 13:
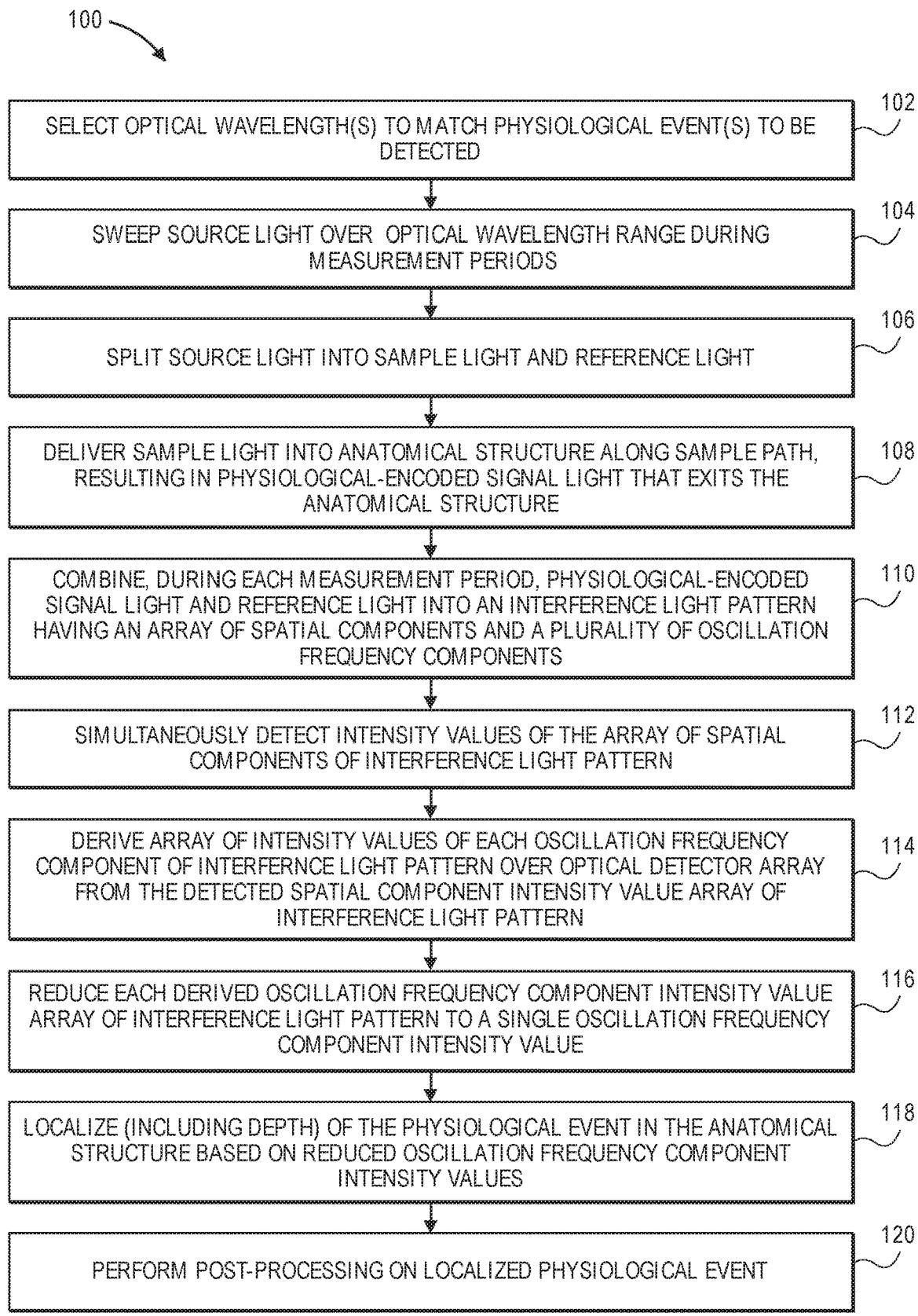
FIG. 13 is a flow diagram illustrating one method used by The non-invasive optical measurement systems of FIG. 1 to non-invasively localize a physiological event within an anatomical structure.

Referring to FIG. 13, having described the structure and function of the non-invasive optical measurement system 10, one particular method 100 performed by the system 10 to non-invasively determine the depth of a physiological event (in this case, a fast-optical signal) in the anatomical structure 12 (in this case, the brain) will now be described.

First, the optical wavelength(s) of the source light 30 is selected to match the physiological event(s) to be detected in the brain 12 (step 102). In this case, the physiological event is a fast-optical signal, and thus, one optical wavelength may be greater than 850 nm. In the case where it is desirable to additionally detect blood oxygen concentration, another optical wavelength may be selected to be in the range of 650 nm to 750 nm.

Next, the controller 26 sends a control signal to the drive circuit of the optical source 20 to repeatedly sweep the source light 30 over the optical wavelength range (e.g., 1050 nm to 1070 nm) during the measurement periods, with each measurement period corresponding to a single optical wavelength range sweep 50 (step 104). As discussed above, each measurement period is preferably equal to or less than the speckle decorrelation time of the brain 12, e.g., equal to or less than 100 microseconds, and preferably, equal to or less than 10 microseconds.

The interferometer 22 (e.g., via the optical beam splitter 42) splits the source light 30 into sample light 32 and reference light 36 (step 106). The interferometer 22 then delivers the sample light 32 into the brain 12 along a single detected optical path bundle 14, such that the sample light 32 is scattered by the brain 12, resulting in physiological-encoded signal light 34 that exits the brain 12 (step 108), and combines, during each of the measurement periods (i.e., each sweep of the optical wavelength sweep 50), the physiological-encoded signal light 34 and the reference light 36 into an interference light pattern 38 having an array of spatial components and a plurality of oscillation frequency components, with oscillation frequency components being respectively encoded with a plurality of different depths in the brain 12 (step 110).

While the optical wavelength of the source light 30 is repeatedly varied over the selected optical wavelength sweep 50, the optical detector array 24 simultaneously detects intensity values I of the array of spatial components of the interference light pattern 38 (i.e., sampled across the optical wavelength range) during the measurement periods (step 112). The processor 28 then derives an array of intensity values I of each oscillation frequency component of the interference light pattern 38 over the optical detector array 24 from the detected spatial component intensity value array of the interference light pattern 38 during one or more of the measurement periods (step 114).

In one technique, the processor 28 accomplishes step 114 in a single measurement period by computing a Fourier transform of the detected spatial component intensity value array of the interference light pattern 38 to acquire the oscillation frequency component intensity value array, e.g., using for example a conventional camera (e.g., a CCD camera) to detect the spatial component intensity value array, and the processor 28 to compute Fourier transform of the detected spatial component intensity value array to acquire the oscillation frequency component intensity value array.

In another technique, the processor 28 accomplishes step 114 over a plurality of measurement periods by deriving each oscillation frequency component intensity value array over the optical detector array 24 from the detected spatial component intensity value array of the interference light pattern 38 during each respective one of the measurement periods. In particular, the processor 28 locks in each oscillation frequency component during each respective one of the measurement periods (e.g., using for example a lock-in camera) by accumulating at least two sequential ones of the intensity values I detected during each cycle of the respective oscillation frequency component respectively in at least two bins, and performing a function on the accumulated contents of the at least two bins (e.g., computing the difference between the accumulated contents of two bins, or computing a quadrature of the accumulated contents of four bins), and outputs the array of intensity values I of each oscillation frequency component over the optical detector array 24.

Next, the processor 28 (e.g., a CPU) reduces each derived oscillation frequency component intensity value array to a single oscillation frequency component intensity value, e.g., by computing a mean of the respective derived oscillation frequency component intensity value array (step 116), and localizes (including determining depth) of the fast-optical signal in the brain 12, at least partially, based on the reduced frequency component intensity values (step 118). In the case where multiple detected optical path bundles 14 through the brain 12 are created using complex source-detector arrangements (e.g., single-source multi-detector, multi-source single-detector, or multi-source multi-detector) to simultaneously create multiple detected optical path bundles 14 spatially separated from each other within the brain 12 in a single measurement period, or by using a movable source-detector arrangement, the processor 28 may also localize the fast-optical signal in an x-y plane along the surface of the brain 12, such that a three-dimensional location of the fast-optical signal within the brain 12 is determined. The processor 28 may then perform post-processing on the localized fast-optical signal, e.g., determining the level and location of neural activity within the brain 12 (step 122).

Figure 14:
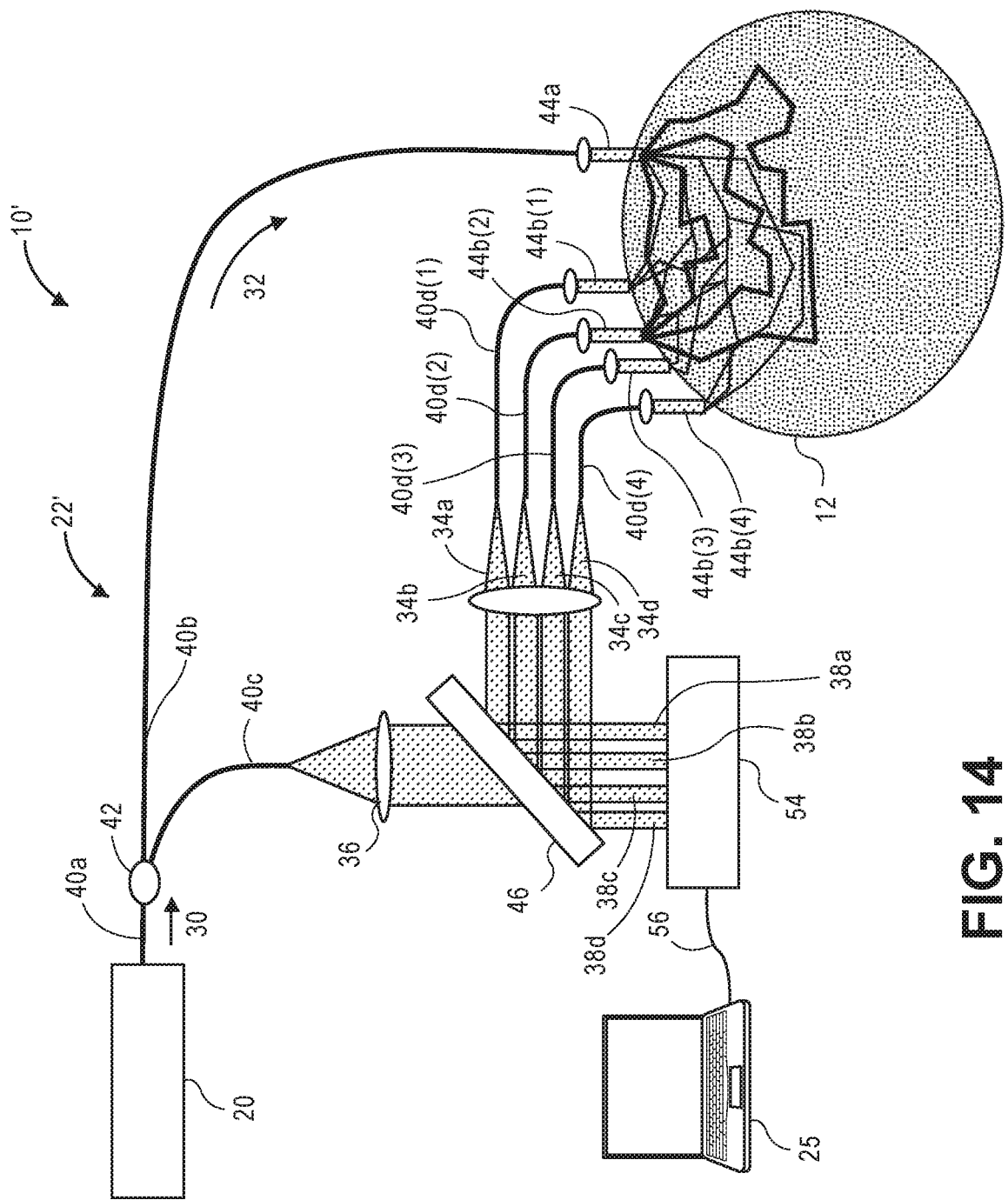
FIG. 14 is a plan view of a non-invasive optical measurement system constructed in accordance with another embodiment of the present inventions.

Referring now to FIG. 14, an optional embodiment of non-invasive optical measurement system 10' constructed in accordance with the present inventions will now be described. The non-invasive optical measurement system 10' is similar to the non-invasive optical measurement system 10 illustrated in FIGS. 1 and 3, with the exception that system 10' is capable of localizing the fast-optical signal in the brain 12 in three dimensions. The system 10' comprises an interferometer 22' that is configured for combining physiological-encoded signal light portions 34*a*-34*d* exiting the brain 12 and the reference light 36 into a plurality of interference light patterns 38*a*-38*d*, and an optical detector array 24 that is topologically divided into a plurality of sub-arrays 24*a*-24*d* (shown in FIG. 15) configured for respectively detecting the spatial component intensity value arrays of the interference light patterns 38*a*-38*d*. The processor 28 is configured for determining a three-dimensional location of the fast-optical signal in the brain 12 based on the detected spatial component intensity value arrays of the respective interference light patterns 38*a*-38*d*.

To this end, the interferometer 22' comprises a plurality of output optical fibers 40*d*(1)-40*d*(4) configured for receiving the neural-encoded signal light portions 34*a*-34*d* from the brain 12 via four respective input ports 44*b*(1)-44*b*(4). Similar to the output optical fiber 40*d* described above in FIG. 3, each of the output optical fibers 40*d*(1)-40*d*(4) may advantageously be multi-mode optical fibers and/or bundles of optical fibers, with the accompanying advantage of boosting light collection efficiency, and leading to higher SNR.

The optical beam combiner 46' is configured for receiving the neural-encoded signal light portions 34*a*-34*d* from the respective output optical fibers 44*b*(1)-44*b*(4), receiving the reference light 36 from the reference arm optical fiber 40*c*, and respectively combining the neural-encoded signal light portions 34*a*-34*d* and reference light 36 via superposition to generate the interference light patterns 38*a*-38*d*, each of which has spatial components and oscillation frequency components, which are respectively encoded with different depths of the brain 12 in the same manner described above with respect to the single interference light pattern 38 in the embodiment of FIG. 3.

Figure 15:
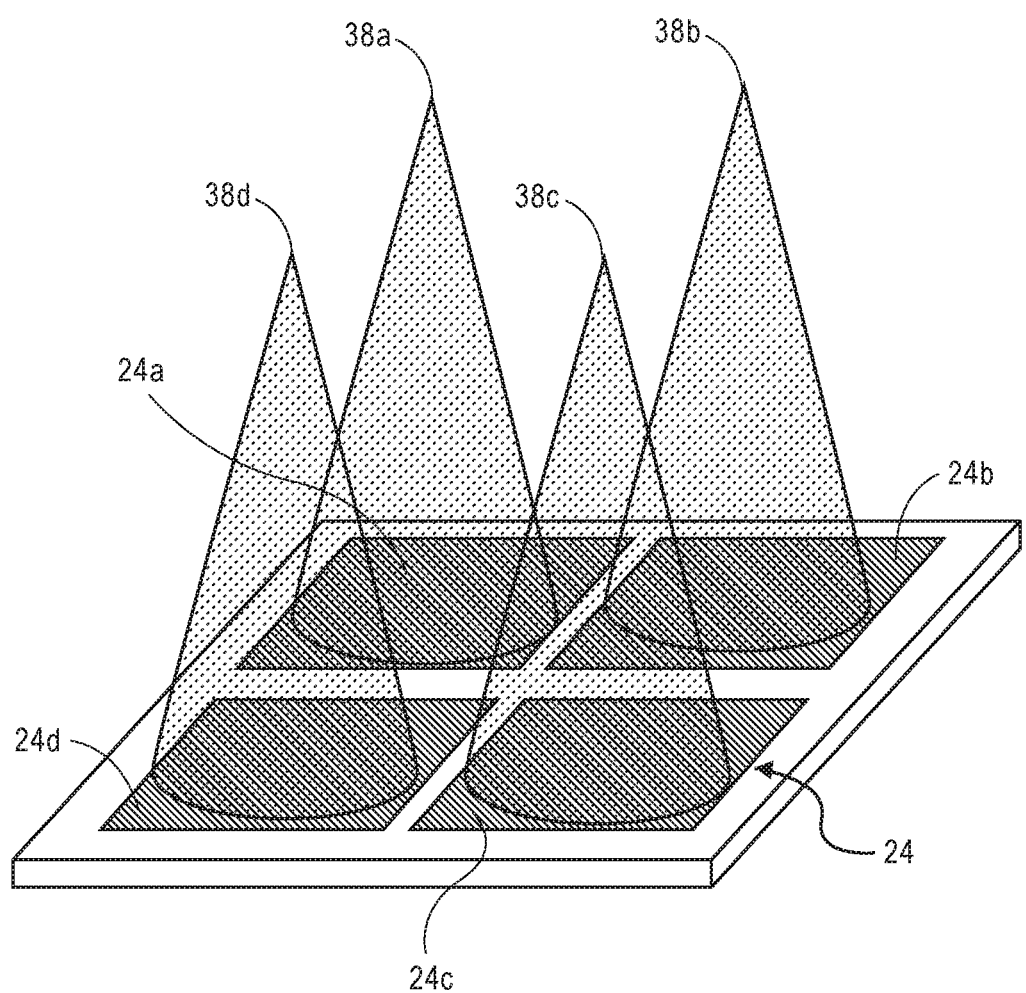
FIG. 15 is a perspective view of an optical detector array used by The non-invasive optical measurement system of FIG. 14.

Referring to FIG. 15, the plurality of sub-arrays 24*a*-24*d* of the optical detector array 24 are respectively configured for detecting an array of intensity values I respectively of the array of spatial components of the interference light patterns 38*a*-38*d* during each measurement period. Although four sub-arrays 24*a*-24*d* are illustrated, it should be appreciated that the optical detector array 24 may be partitioned into any plural number of sub-arrays, preferably, a number that matches the number of interference light patterns 38 generated. As with the optical detector array 24 described above in FIGS. 1 and 3, the optical detector array 24 may be implemented as a camera with a frame rate that can be controlled by the controller 26 (shown in FIG. 1) in coordination with the optical wavelength sweeps of the optical source 20 to match the measurement period, and has the same advantages of increasing the SNR of the detection of the spatial component intensity values I relative to a conventional iNIRS system that uses a single large detector.

The processor 28 is configured for determining a three-dimensional location of the fast-optical signal in the brain 12 based on the detected spatial component intensity values I of the respective interference light patterns 38*a*-38*d*, with two of the dimensions represented as the plane spanning the surface of the brain 12 and the third dimension as the depth into the brain 12. The depth of the fast-optical signal in the brain 12 can be determined using any one of the other techniques described above, with the only difference being that the depths of the fast-optical signal in the brain 12 are determined on a spatial region-by-spatial region basis.

Thus, the processor 28 is configured for deriving oscillation frequency component intensity value arrays for each sub-array 24*a*-24*d* of the optical detector array 24 from the detected spatial component intensity arrays of the respective interference light patterns 38*a*-38*d* during the measurement periods (i.e., first oscillation frequency component intensity value arrays are derived over the sub-array 24*a* of the optical detector array 24, second oscillation frequency component intensity value arrays are derived over the sub-array 24*b* of the optical detector array 24, third oscillation frequency component intensity value arrays are derived over the sub-array 24*c* of the optical detector array 24, and fourth oscillation frequency component intensity value arrays are derived over the sub-array 24d of the optical detector array 24, and so forth).

The processor 28 can perform this function using the other techniques described above, e.g., by using a conventional camera to continuously sample the spatial component intensity value array of each of the interference light patterns 28a-28d at a set frequency, and a CPU to compute the Fourier transform of the spatial component intensity value arrays to obtain the oscillation frequency component intensity value arrays, or by using a lock-in camera to lock in different oscillation frequency components respectively during a plurality of measurement periods to obtain the oscillation frequency component intensity value arrays.

The processor 28 is further configured for reducing (e.g., by computing a mean) each oscillation frequency component intensity value array to a single oscillation frequency component value for each of the sub-arrays 24a-24d of the optical detector array 24, and determining the depth of the fast-optical signal in the brain 12, at least partially, based on the reduced oscillation frequency component intensity values. The depth of the fast-optical signal in the brain 12 can be determined, e.g., using the technique described above with respect to FIGS. 6A and 6B, while the location of the fast-optical signal along the surface of the brain 12 may be geometrically determined based on the strength of the fast-optical signal detected at the spatial regions of the brain 12 as correlated to the sub-arrays 24a-24d of the optical detector array 24.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A non-invasive optical measurement system, comprising:
   an optical source configured for sweeping a source light over a range of optical wavelengths during each of at least one measurement period;
   an interferometer configured for splitting the source light into sample light and reference light, delivering the sample light into an anatomical structure, such that the sample light is scattered by the anatomical structure, resulting in physiological-encoded signal light that exits the anatomical structure, and combining, during each of the at least one measurement period, the physiological-encoded signal light and the reference light into an interference light pattern having an array of spatial components and a plurality of oscillation frequency components, the plurality of oscillation frequency components respectively encoded with a plurality of different depths of the anatomical structure;
   an optical detector array configured for detecting intensity values of the array of spatial components of the interference light pattern during each of the at least one measurement period, the optical detector array comprising an M×N array of optical detectors, wherein each of M and N is greater than one; and
   a processor configured for sequentially deriving an array of intensity values of each oscillation frequency component of the interference light pattern over the optical detector array from the detected spatial component intensity value array of the interference light pattern during the at least one measurement period, reducing each derived oscillation frequency component intensity value array to a single frequency component intensity value by computing a mean of the respective derived oscillation frequency component intensity value array over at least two optical detectors of the optical detector array oriented in an M-direction and at least two optical detectors of the optical detector array oriented in an N-direction, and determining a depth of a physiological event in the anatomical structure, at least partially, based on the reduced frequency component intensity values.

2. The non-invasive optical measurement system of claim 1, wherein the anatomical structure is a brain.

3. The non-invasive optical measurement system of claim 2, wherein the physiological event is indicative of neural activity.

4. The non-invasive optical measurement system of claim 3, wherein the physiological event is a fast-optical signal.

5. The non-invasive optical measurement system of claim 1, wherein each of the at least one measurement period is equal to or less than a speckle decorrelation time of the anatomical structure.

6. The non-invasive optical measurement system of claim 1, wherein each of the at least one measurement period is equal to or less than 100 microseconds.

7. The non-invasive optical measurement system of claim 1, wherein each of the at least one measurement period is equal to or less than 10 microseconds.

8. The non-invasive optical measurement system of claim 1, wherein the processor is configured for determining the depth of the physiological event in the anatomical structure, at least partially, by comparing the reduced oscillation frequency component intensity values to corresponding reference oscillation frequency component intensity values.

9. The non-invasive optical measurement system of claim 1, wherein the at least one measurement period comprises a single measurement period, and wherein the processor is configured for sequentially deriving each oscillation frequency component intensity array over the optical detector array from the detected spatial component intensity value array of the interference light pattern during the single measurement period by computing a Fourier transform of the detected spatial component intensity value array of the interference light pattern.

10. The non-invasive optical measurement system of claim 9, further comprising a charged coupled device (CCD) camera comprising the optical detector array.

11. The non-invasive optical measurement system of claim 1, wherein the at least one measurement period comprises a plurality of measurement periods, and wherein the processor is configured for sequentially deriving each oscillation frequency component intensity value array over the optical detector array from the detected spatial component intensity value array of the interference light pattern during each respective one of the measurement periods.

12. The non-invasive optical measurement system of claim 11, wherein the processor is configured for sequentially deriving each oscillation frequency component intensity value array over the optical detector array from the detected spatial component intensity value array of the interference light pattern during each respective one of the measurement periods by locking in each oscillation frequency component during each respective one of the measurement periods.

13. The non-invasive optical measurement system of claim 12, wherein the processor is configured for locking in each oscillation frequency component during each respective one of the measurement periods by accumulating at least two sequential ones of the intensity values detected during each cycle of the respective oscillation frequency component respectively in at least two bins, and performing a function on the accumulated contents of the at least two bins.

14. The non-invasive optical measurement system of claim 13, wherein the at least two bins comprises only two bins, and the function is computing the difference between the accumulated contents of the two bins.

15. The non-invasive optical measurement system of claim 13, wherein the at least two bins comprises only four bins, and the function is computing a quadrature of the accumulated contents of the four bins.

16. The non-invasive optical measurement system of claim 12, further comprising a lock-in camera that includes the optical detector array and a portion of the processor that is configured for locking in each oscillation frequency component during each respective one of the measurement periods.

17. The non-invasive optical measurement system of claim 16, further comprising a central processing unit (CPU) that includes another portion of the processor that is configured for reducing the derived array of intensity values of each oscillation frequency component to the single frequency component value, and determining the depth of the physiological event in the anatomical structure, at least partially, based on the reduced frequency component values.

18. The non-invasive optical measurement system of claim 1, wherein the interference light pattern is a speckle light pattern, and the spatial components are speckle grains.

19. The non-invasive optical measurement system of claim 1, wherein the optical source light has a spectral linewidth of less than 2 pm.

20. The non-invasive optical measurement system of claim 1, wherein the optical source light has a spectral linewidth of less than 0.5 pm.

21. The non-invasive optical measurement system of claim 1, wherein the optical wavelength range is greater than 3 pm.

22. The non-invasive optical measurement system of claim 1, wherein the optical wavelength range is greater than 30 pm.

23. The non-invasive optical measurement system of claim 1, wherein the mean of the respective derived oscillation frequency component intensity value array is computed over all optical detectors of the optical detector array.

24. A non-invasive optical measurement method, comprising:
sweeping a source light over a range of optical wavelengths during each of at least one measurement period;
splitting the source light into sample light and reference light;
delivering the sample light into an anatomical structure, such that the sample light is scattered by the anatomical structure, resulting in physiological-encoded signal light that exits the anatomical structure;
combining, during each of the at least one measurement period, the physiological-encoded signal light and the reference light into an interference light pattern having an M×N array of spatial components and a plurality of oscillation frequency components, the plurality of oscillation frequency components respectively encoded with a plurality of different depths of the anatomical structure, wherein each of M and N is greater than one;
detecting intensity values of the array of spatial components of the interference light pattern during each of the at least one measurement period;
sequentially deriving an array of intensity values of each oscillation frequency component of the interference light pattern from the detected spatial component intensity value array of the interference light pattern during the at least one measurement period;
reducing each derived oscillation frequency component intensity value array to a single oscillation frequency component intensity value by computing a mean of the respective derived oscillation frequency component intensity value array over at least two of the array of spatial components oriented in an M-direction and at least two of the array of spatial components oriented in an N-direction; and
determining a depth of a physiological event in the anatomical structure, at least partially, based on the reduced oscillation frequency component intensity values.

25. The non-invasive optical measurement method of claim 24, wherein the anatomical structure is a brain.

26. The non-invasive optical measurement method of claim 25, wherein the physiological event is indicative of neural activity.

27. The non-invasive optical measurement method of claim 26, wherein the physiological event is a fast-optical signal.

28. The non-invasive optical measurement method of claim 24, wherein each of the at least one measurement period is equal to or less than a speckle decorrelation time of the anatomical structure.

29. The non-invasive optical measurement method of claim 24, wherein each of the at least one measurement period is equal to or less than 100 microseconds.

30. The non-invasive optical measurement method of claim 24 wherein each of the at least one measurement period is equal to or less than 10 microseconds.

31. The non-invasive optical measurement method of claim 24, wherein the depth of the physiological event in the anatomical structure is determined, at least partially, by comparing the reduced oscillation frequency component intensity values to corresponding reference oscillation frequency component intensity values.

32. The non-invasive optical measurement method of claim 24, wherein the at least one measurement period comprises a single measurement period, and wherein each oscillation frequency component intensity value array is derived from the detected spatial component intensity value array of the interference light pattern during the single measurement period by computing a Fourier transform of the detected spatial component intensity value array of the interference light pattern.

33. The non-invasive optical measurement method of claim 32, wherein the spatial component intensity value array of the interference light pattern is detected during each of the at least one measurement period using a charged coupled device (CCD) camera.

34. The non-invasive optical measurement method of claim 24, wherein the at least one measurement period comprises a plurality of measurement periods, and wherein each oscillation frequency component intensity value array is derived from the detected spatial component intensity value array of the interference light pattern during each respective one of the measurement periods.

35. The non-invasive optical measurement method of claim 34, wherein each oscillation frequency component is locked in during each respective one of the measurement periods by accumulating at least two sequential ones of the intensity values detected during each cycle of the respective oscillation frequency component respectively in at least two bins, and performing a function on the accumulated contents of the at least two bins.

36. The non-invasive optical measurement method of claim 35, wherein the at least two bins comprises only two bins, and the function is computing the difference between the accumulated contents of the two bins.

37. The non-invasive optical measurement method of claim 35, wherein the at least two bins comprises only four bins, and the function is computing a quadrature of the accumulated contents of the four bins.

38. The non-invasive optical measurement method of claim 24, wherein the interference light pattern is a speckle light pattern, and the spatial components are speckle grains.

39. The non-invasive optical measurement method of claim 24, wherein the optical source light has a spectral linewidth of less than 2 pm.

40. The non-invasive optical measurement method of claim 24, wherein the optical source light has a spectral linewidth of less than 0.5 pm.

41. The non-invasive optical measurement method of claim 24, wherein the optical wavelength range is greater than 3 pm.

42. The non-invasive optical measurement method of claim 24, wherein the optical wavelength range is greater than 30 pm.

43. The non-invasive optical measurement method of claim 24, wherein the mean of the respective derived oscillation frequency component intensity value array is computed over all of the array of spatial components.

* * * * *